US011666926B2

(12) United States Patent
Nguyen et al.

(10) Patent No.: US 11,666,926 B2
(45) Date of Patent: Jun. 6, 2023

(54) COLLECTION OF MONONUCLEAR CELLS UPON MID-PROCEDURE TERMINATION

(71) Applicant: Fenwal, Inc., Lake Zurich, IL (US)

(72) Inventors: Lan T. Nguyen, Vernon Hills, IL (US); Zahra R. Ali, Chicago, IL (US); Angela N. Carlson, Arlington Heights, IL (US); Korri Hershenhouse, Glenview, IL (US); Molly Erickson, Colorado Springs, CO (US)

(73) Assignee: Fenwal, Inc., Lake Zurich, IL (US)

( * ) Notice: Subject to any disclaimer, the term of this patent is extended or adjusted under 35 U.S.C. 154(b) by 331 days.

(21) Appl. No.: 17/143,267

(22) Filed: Jan. 7, 2021

(65) Prior Publication Data
US 2021/0129159 A1    May 6, 2021

Related U.S. Application Data

(63) Continuation of application No. 16/226,740, filed on Dec. 20, 2018, now Pat. No. 10,919,049.

(Continued)

(51) Int. Cl.
*B04B 5/04*    (2006.01)
*A61M 1/36*    (2006.01)
(Continued)

(52) U.S. Cl.
CPC ............. *B04B 5/0442* (2013.01); *A61M 1/02* (2013.01); *A61M 1/304* (2014.02);
(Continued)

(58) Field of Classification Search
CPC ....... B04B 5/0442; A61M 1/02; A61M 1/304; A61M 1/3672; A61M 1/3683;
(Continued)

(56) References Cited

U.S. PATENT DOCUMENTS 5,316,667 A    5/1994 Brown et al.
5,462,416 A    10/1995 Dennehey et al.
(Continued)

FOREIGN PATENT DOCUMENTS

DE    102005001779 B4    12/2009
EP        3 235 527 A1    10/2017
WO    WO 2016/205511 A1    12/2016

OTHER PUBLICATIONS

Extended European Search Report For European Patent Application No. 18214293.5, dated May 8, 2019.

*Primary Examiner* — Shuyi S. Liu
(74) *Attorney, Agent, or Firm* — Cook Alex Ltd.

(57) ABSTRACT

Mid-procedure termination of a mononuclear cell collection procedure may prevent collection of an amount of red blood cells that is required to harvest a complete mononuclear cell product. Blood separation systems and methods are provided for minimizing the impact of or recovering from mid-procedure termination of such a mononuclear cell collection procedure. According to one approach, blood or separated red blood cells are conveyed into a red blood cell collection container relatively early in the procedure to minimize the impact of a later termination of the procedure. According to another approach, blood and/or separated red blood cells within a fluid processing assembly are redirected through the fluid processing assembly following mid-procedure termination to allow for at least partial mononuclear cell collection. According to yet another approach, a double-needle fluid processing assembly may be converted into a single-needle configuration to allow for continued processing following mid-procedure termination.

20 Claims, 11 Drawing Sheets

Related U.S. Application Data

(60) Provisional application No. 62/609,392, filed on Dec. 22, 2017.

(51) Int. Cl.
 *A61M 1/30* (2006.01)
 *A61M 1/02* (2006.01)

(52) U.S. Cl.
 CPC ........ *A61M 1/3672* (2013.01); *A61M 1/3683* (2014.02); *A61M 1/3693* (2013.01); *A61M 1/3696* (2014.02); *A61M 1/30* (2013.01); *A61M 1/36* (2013.01)

(58) Field of Classification Search
 CPC .... A61M 1/3693; A61M 1/3696; A61M 1/30; A61M 1/36
 See application file for complete search history.

(56) References Cited

U.S. PATENT DOCUMENTS

| | | |
|---|---|---|
| 5,632,893 A | 5/1997 | Brown et al. |
| 5,868,696 A | 2/1999 | Giesler et al. |
| 5,980,760 A | 11/1999 | Min et al. |
| 6,312,607 B1 | 11/2001 | Brown et al. |
| 2002/0041825 A1 | 4/2002 | Scheuner et al. |
| 2010/0217174 A1 | 8/2010 | Min |
| 2014/0057771 A1 | 2/2014 | Case et al. |
| 2014/0174542 A1 | 6/2014 | Jansson et al. |
| 2015/0115180 A1* | 4/2015 | Schoonover ........ A61M 1/3437 250/565 |
| 2015/0219558 A1 | 8/2015 | Koudelka et al. |
| 2017/0007758 A1* | 1/2017 | Kimura ............... A61M 1/0218 |

\* cited by examiner

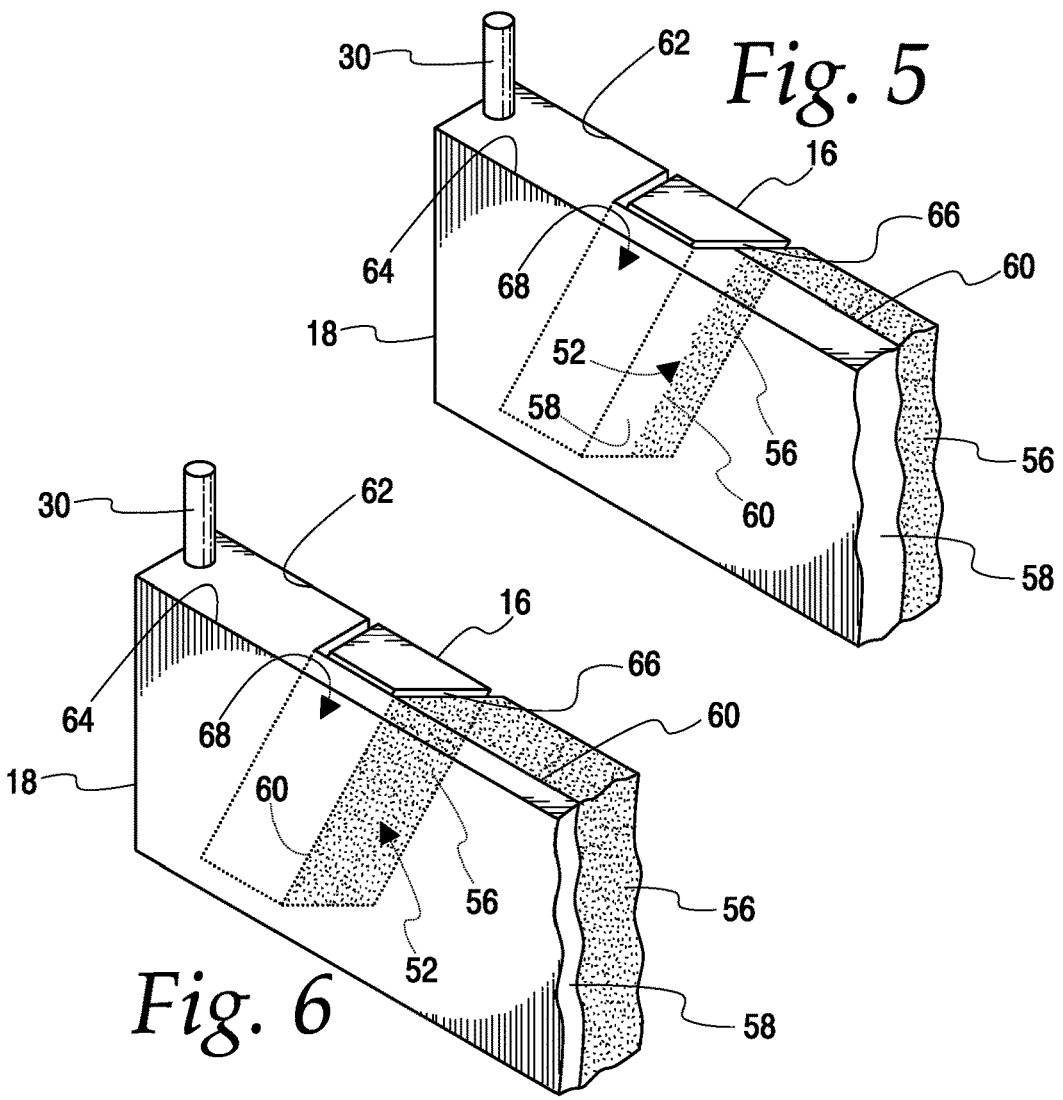
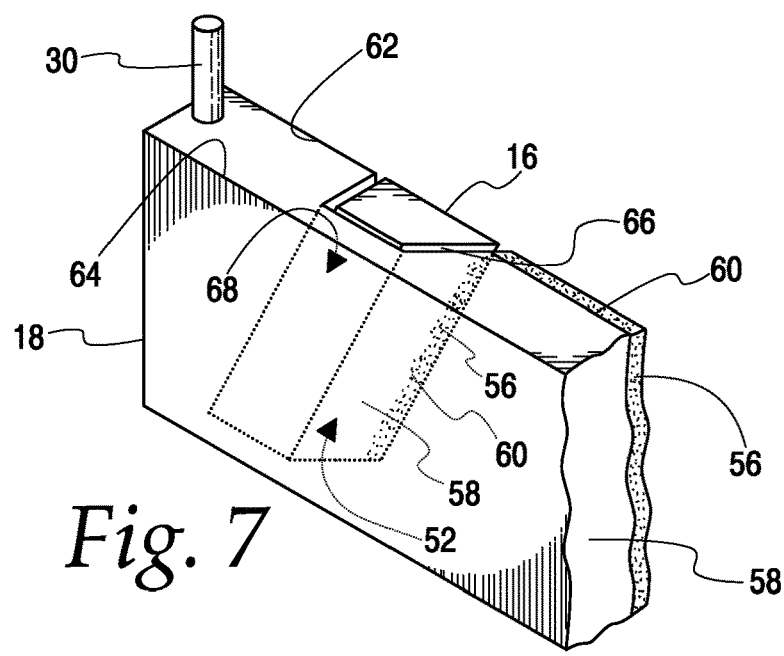

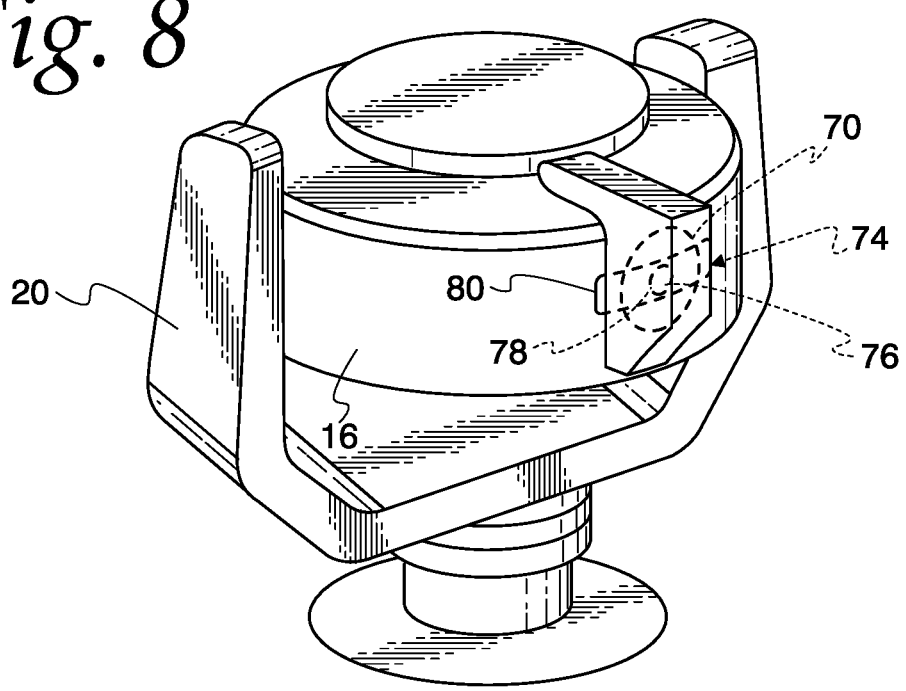
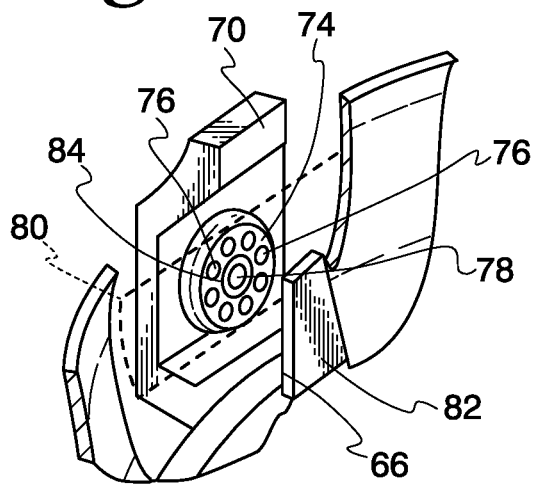
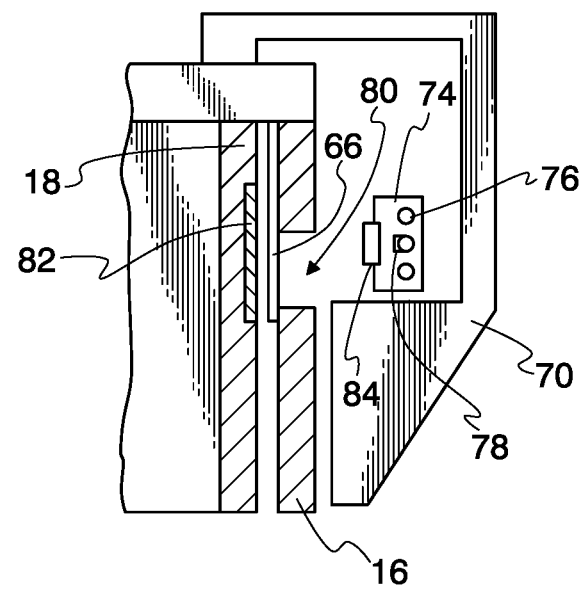

COLLECTION OF MONONUCLEAR CELLS UPON MID-PROCEDURE TERMINATION

CROSS-REFERENCE TO RELATED APPLICATIONS

This application is a continuation of U.S. patent application Ser. No. 16/226,740, filed Dec. 20, 2018, which claims the benefit of and priority of U.S. Provisional Patent Application Ser. No. 62/609,392, filed Dec. 22, 2017, the contents of which are incorporated by reference herein.

BACKGROUND

Field of the Disclosure

The present disclosure relates to collection of mononuclear cells. More particularly, the present disclosure relates to collection of mononuclear cells in a terminated collection procedure.

Description of Related Art

Various blood processing systems now make it possible to collect particular blood constituents, rather than whole blood, from donors or patients or other blood sources. Typically, in such systems, whole blood is drawn from a source, the particular blood component or constituent is removed and collected, and the remaining blood constituents are returned to the source. By thus removing only particular constituents, potentially less time is needed for the source's body to return to normal (in the case of a living source), and donations can be made at more frequent intervals than when whole blood is collected. This increases the overall supply of blood constituents, such as plasma and platelets, made available for health care.

Whole blood is typically separated into its constituents through centrifugation. This requires that the whole blood be passed through a centrifuge after it is withdrawn from, and before it is returned to, the source. To avoid contamination and possible infection of the source, the blood is preferably contained within a sealed, sterile fluid flow system during the entire centrifugation process. Typical blood processing systems thus include a permanent, reusable centrifuge assembly containing the hardware (drive system, pumps, valve actuators, programmable controller, and the like) that spins and pumps the blood, and a disposable, sealed and sterile fluid processing assembly that is mounted in cooperation on the hardware. The centrifuge assembly engages and spins a disposable centrifuge chamber of the fluid processing assembly during a collection procedure. The blood, however, makes actual contact only with the fluid processing assembly, which assembly is used only once and then discarded.

As the whole blood is spun by the centrifuge, the heavier (greater specific gravity) components, such as red blood cells, move radially outwardly away from the center of rotation toward the outer or "high-G" wall of the separation chamber. The lighter (lower specific gravity) components, such as plasma, migrate toward the inner or "low-G" wall of the separation chamber. Various ones of these components can be selectively removed from the whole blood by forming appropriately located channeling seals and outlet ports in the separation chamber.

An exemplary method of centrifugally separating and collecting mononuclear cells ("MNCs") is described in U.S. Pat. No. 5,980,760, which is incorporated herein by reference. In such a procedure, whole blood in a centrifuge is separated into platelet-poor plasma, an interface or MNC-containing layer, and packed red blood cells. The platelet-poor plasma is collected for later use, while the packed red blood cells are returned to the blood source and the MNC-containing layer remains in the centrifuge. When a target amount of platelet-poor plasma has been collected, an MNC accumulation phase begins. During this phase, the position of the interface within the centrifuge is moved closer to the low-G wall, such that platelet-rich plasma and packed red blood cells are removed from the centrifuge while the MNC-containing layer continues to build up in the centrifuge. Portions of the platelet-rich plasma and the packed red blood cells are returned to the blood source, with the remainder of the platelet-rich plasma and packed red blood cells being recirculated through the centrifuge to maintain a proper hematocrit.

When a certain amount of blood has been processed, the return and recirculation of the packed red cells is ended and a red blood cell collection phase begins. During this phase, recirculation and return of the platelet-rich plasma continues, while the packed red blood cells are conveyed from the centrifuge to a red blood cell collection container for later use.

When a target amount of packed red blood cells has been collected, an MNC harvest phase begins. To harvest the MNCs in the MNC-containing layer, the packed red blood cells are temporarily prevented from exiting the centrifuge. At least a portion of the collected red blood cells is conveyed into the centrifuge, which forces the MNC-containing layer to exit the centrifuge via the same outlet as the platelet-rich plasma. The platelet-rich plasma exiting the centrifuge ahead of the MNC-containing layer is directed into the platelet-poor plasma container, with the MNC-containing layer subsequently being directed into an MNC collection container.

Following the MNC harvest phase, a plasma flush phase begins. During this phase, plasma from the platelet-poor plasma container is used to flush any MNC-containing layer positioned between the separation chamber and the MNC collection container back into the separation chamber. The MNC-containing layer flushed back into the separation chamber may be subsequently collected by repeating the various phases, until a target amount of MNC product has been collected. Following collection, the MNC product may be treated to further processing, such as extracorporeal photopheresis.

For any of a number of reasons, the MNC-collection procedure may be terminated mid-process. If a sufficient amount of packed red blood cells has not been collected at the time of termination, the MNC-containing layer cannot be fully harvested using conventional techniques. Accordingly, it would be advantageous to provide alternative approaches to MNC collection to allow for more complete collection of the MNC-containing layer in the event of mid-process termination.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a method is provided for collecting mononuclear cells. The method includes, separating red blood cells from blood in a separation chamber and conveying at least a portion of the separated red blood cells from the separation chamber to a red blood cell collection container. A mononuclear cell-containing layer is separated from blood in the separation chamber while red blood cells are removed from the separation chamber. At least a portion of the removed red blood cells is recirculated through the separation chamber, while allowing a volume of the mononuclear cell-containing layer to increase in the separation chamber. At least a portion of the contents of the red blood cell collection container is conveyed to the separation chamber to convey at least a portion of the mononuclear cell-containing layer out of the separation chamber for collection, with the separated red blood cells being conveyed to the red blood cell collection container prior to recirculating the removed red blood cells through the separation chamber.

In another aspect, a fluid processing system includes a centrifuge configured to receive a separation chamber of a fluid processing assembly. The fluid processing system also includes a plurality of pumps configured to convey fluids through the fluid processing assembly. A controller of the fluid processing system is programmed to actuate the centrifuge to separate red blood cells from blood in the separation chamber and actuate at least one of the plurality of pumps to convey at least a portion of the separated red blood cells from the separation chamber to a red blood cell collection container of the fluid processing assembly. The controller is further programmed to actuate the centrifuge to separate a mononuclear cell-containing layer from blood in the separation chamber while actuating at least one of the plurality of pumps to remove red blood cells from the separation chamber, actuating at least one of the plurality of pumps to recirculate at least a portion of the removed red blood cells through the separation chamber, and allowing a volume of the mononuclear cell-containing layer to increase in the separation chamber. The controller is also programmed to actuate at least one of the plurality of pumps to convey at least a portion of the contents of the red blood cell collection container to the separation chamber to convey at least a portion of the mononuclear cell-containing layer out of the separation chamber for collection, with the controller being programmed such that the separated red blood cells are conveyed to the red blood cell collection container prior to recirculating the removed red blood cells through the separation chamber.

In yet another aspect, a method is provided for collecting mononuclear cells. The method includes conveying blood to a red blood cell collection container; separating a mononuclear cell-containing layer from blood in a separation chamber while removing red blood cells from the separation chamber. At least a portion of the removed red blood cells is recirculated through the separation chamber, while allowing a volume of the mononuclear cell-containing layer to increase in the separation chamber. At least a portion of the contents of the red blood cell collection container is conveyed to the separation chamber to convey at least a portion of the mononuclear cell-containing layer out of the separation chamber for collection, with blood being conveyed to the red blood cell collection container prior to recirculating the removed red blood cells through the separation chamber.

In another aspect, a fluid processing system includes a centrifuge configured to receive a separation chamber of a fluid processing assembly, along with a plurality of pumps configured to convey fluids through the fluid processing assembly. A controller of the fluid processing system is programmed to actuate at least one of the plurality of pumps to convey blood to a red blood cell collection container of the fluid processing assembly. The controller is further programmed to actuate the centrifuge to separate a mononuclear cell-containing layer from blood in the separation chamber while actuating at least one of the plurality of pumps to remove red blood cells from the separation chamber, actuating at least one of the plurality of pumps to recirculate at least a portion of the removed red blood cells through the separation chamber, and allowing a volume of the mononuclear cell-containing layer to increase in the separation chamber. The controller is also programmed to actuate at least one of the plurality of pumps to convey at least a portion of the contents of the red blood cell collection container to the separation chamber to convey at least a portion of the mononuclear cell-containing layer out of the separation chamber for collection, with the controller being programmed such that blood is conveyed to the red blood cell collection container prior to recirculating the removed red blood cells through the separation chamber.

In yet another aspect, a method is provided for collecting mononuclear cells. The method includes conveying blood through a cassette and a drip chamber of a fluid processing assembly to a separation chamber of the fluid processing assembly. A mononuclear cell-containing layer is separated from the blood in the separation chamber, with other blood components being removed from the separation chamber while a volume of the mononuclear cell-containing layer increases in the separation chamber. Blood from the cassette and/or the drip chamber is conveyed to a red blood cell collection container of the fluid processing assembly, with at least a portion of the contents of the red blood cell collection container being conveyed to the separation chamber to convey at least a portion of the mononuclear cell-containing layer out of the separation chamber for collection.

In another aspect, a fluid processing system includes a centrifuge configured to receive a separation chamber of a fluid processing assembly, along with a plurality of pumps configured to convey fluids through the fluid processing assembly. A controller of the fluid processing assembly is programmed to actuate at least one of the plurality of pumps to convey blood through a cassette and a drip chamber of the fluid processing assembly to the separation chamber. The controller is further programmed to actuate the centrifuge to separate a mononuclear cell-containing layer from blood in the separation chamber, while actuating at least one of the plurality of pumps to remove other blood components from the separation chamber and allowing a volume of the mononuclear cell-containing layer to increase in the separation chamber. The controller is also programmed to actuate at least one of the plurality of pumps to convey blood from the cassette and/or the drip chamber to a red blood cell collection container of the fluid processing assembly, and actuate at least one of the plurality of pumps to convey at least a portion of the contents of the red blood cell collection container to the separation chamber to convey at least a portion of the mononuclear cell-containing layer out of the separation chamber for collection.

In yet another aspect, a method is provided for collecting mononuclear cells. The method includes conveying blood through a first cassette of a fluid processing assembly to a separation chamber of the fluid processing assembly. A mononuclear cell-containing layer and red blood cells are separated from the blood in the separation chamber, with at least a portion of the red blood cells being conveyed out of the separation chamber and through a second cassette of the fluid processing assembly while a volume of the mononuclear cell-containing layer increases in the separation chamber. Saline is conveyed through the first cassette and/or the second cassette to convey blood and/or red blood cells from the first cassette and/or the second cassette to a red blood cell collection container of the fluid processing assembly, with at least a portion of the contents of the red blood cell collection container being conveyed to the separation chamber to convey at least a portion of the mononuclear cell-containing layer out of the separation chamber for collection.

In another aspect, a fluid processing system includes a centrifuge configured to receive a separation chamber of a fluid processing assembly, along with a plurality of pumps configured to convey fluids through the fluid processing assembly. A controller of the fluid processing system is programmed to actuate at least one of the plurality of pumps to convey blood through a first cassette of a fluid processing assembly to the separation chamber. The controller is further programmed to actuate the centrifuge to separate a mononuclear cell-containing layer and red blood cells from blood in the separation chamber while actuating at least one of the plurality of pumps to convey at least a portion of the red blood cells out of the separation chamber and through a second cassette of the fluid processing assembly, allowing a volume of the mononuclear cell-containing layer to increase in the separation chamber. The controller is also programmed to actuate at least one of the plurality of pumps to convey saline through the first cassette and/or the second cassette to convey blood and/or red blood cells from the first cassette and/or the second cassette to a red blood cell collection container of the fluid processing assembly, with at least one of the plurality of pumps being actuated to convey at least a portion of the contents of the red blood cell collection container to the separation chamber, which conveys at least a portion of the mononuclear cell-containing layer out of the separation chamber for collection.

In yet another aspect, a fluid processing assembly is provided, with the fluid processing assembly being configured for use in combination with a fluid processing system. The fluid processing assembly includes a separation chamber configured to separate a fluid into two or more fluid components, with the separation chamber having an inlet flow path and an outlet flow path. A draw line is provided in fluid communication with the inlet flow path and configured for direct connection to a source to draw a fluid from the source into the fluid processing assembly, while a return line is provided in fluid communication with the outlet flow path and configured for direct connection to the source to convey a replacement fluid and/or at least a portion of a separated fluid component to the source. The draw line includes a first connector, while the return line includes a second connector configured to be connected to the first connector, with connection of the first and second connectors removing one of the draw and return lines from direct connection to the source while placing the other one of the draw and return lines into condition for drawing fluid from the source into the fluid processing assembly and conveying a replacement fluid and/or at least a portion of a separated fluid component to the source.

In another aspect, a method is provided for processing a fluid. The method includes directly connecting a draw line and a return line of a fluid processing assembly to a source, drawing fluid from the source into the fluid processing assembly via the draw line, and processing at least a portion of the fluid within the fluid processing assembly. The processing of the fluid is paused, followed by the draw line and the return line being directly connected so as to remove one of the draw and return lines from direct connection to the source. Thereafter, processing of the fluid is unpaused.

In yet another aspect, a method is provided for processing a fluid. The method includes providing a fluid processing assembly having a draw line and a return line each configured to be directly connected to a source. The draw line and the return line are directly connected so as to prevent one of the draw and return lines from being directly connected to the source. The other one of the draw and return lines is directly connected to the source, followed by fluid being drawn from the source, with at least a portion of the fluid being processed within the fluid processing assembly.

BRIEF DESCRIPTION OF THE DRAWINGS

FIG. 5 is an enlarged perspective view of an interface ramp carried by the centrifuge in association with the separation chamber, showing the centrifugally separated red blood cell layer, plasma layer, and interface within the separation chamber when in a desired location on the ramp;

FIG. 6 is an enlarged perspective view of the interface ramp shown in FIG. 5, showing the red blood cell layer and interface at an undesired high location on the ramp;

FIG. 7 is an enlarged perspective view of the interface ramp shown in FIG. 5, showing the red blood cell layer and interface at an undesired low location on the ramp;

FIG. 8 is a side perspective view of the bowl and spool of the centrifuge when in the operating position, showing a viewing head, which forms a part of an interface controller, being carried by the centrifuge to view the interface ramp during rotation of the bowl;

FIG. 9 is a perspective view of the viewing head, with portions broken away and in section, showing the light source and light detector, which are carried by the viewing head, in alignment with the interface ramp, as viewed from within the spool and bowl of the centrifuge;

FIG. 10 is a side section view of the bowl, spool, and viewing head when the viewing head is aligned with the interface ramp;

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 1:
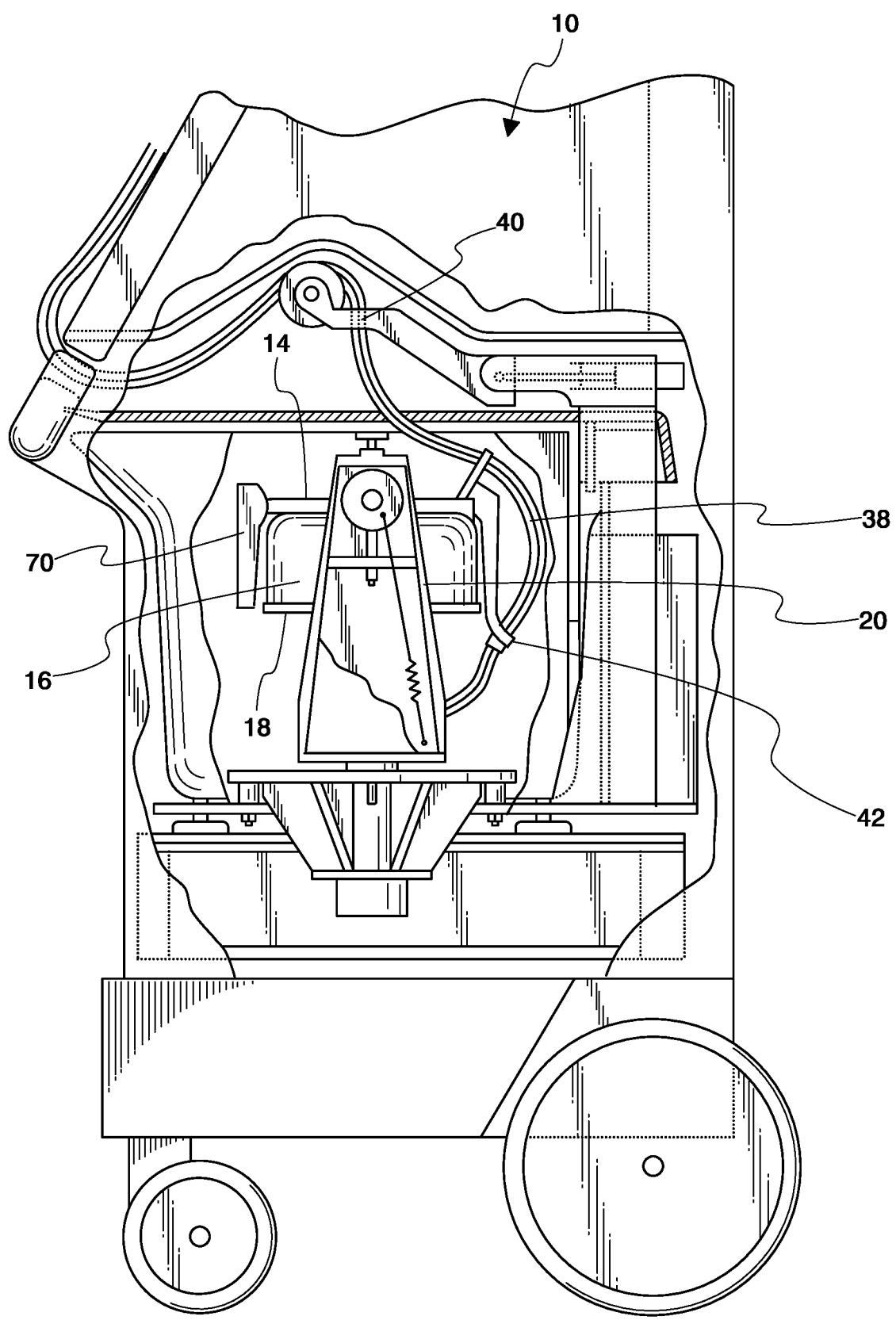
FIG. 1 is a side elevation view, with portions broken away and in section, of a centrifugal fluid processing system employing aspects of the present disclosure, with a centrifuge bowl and spool of the system being shown in their operating position.
Figure 2:
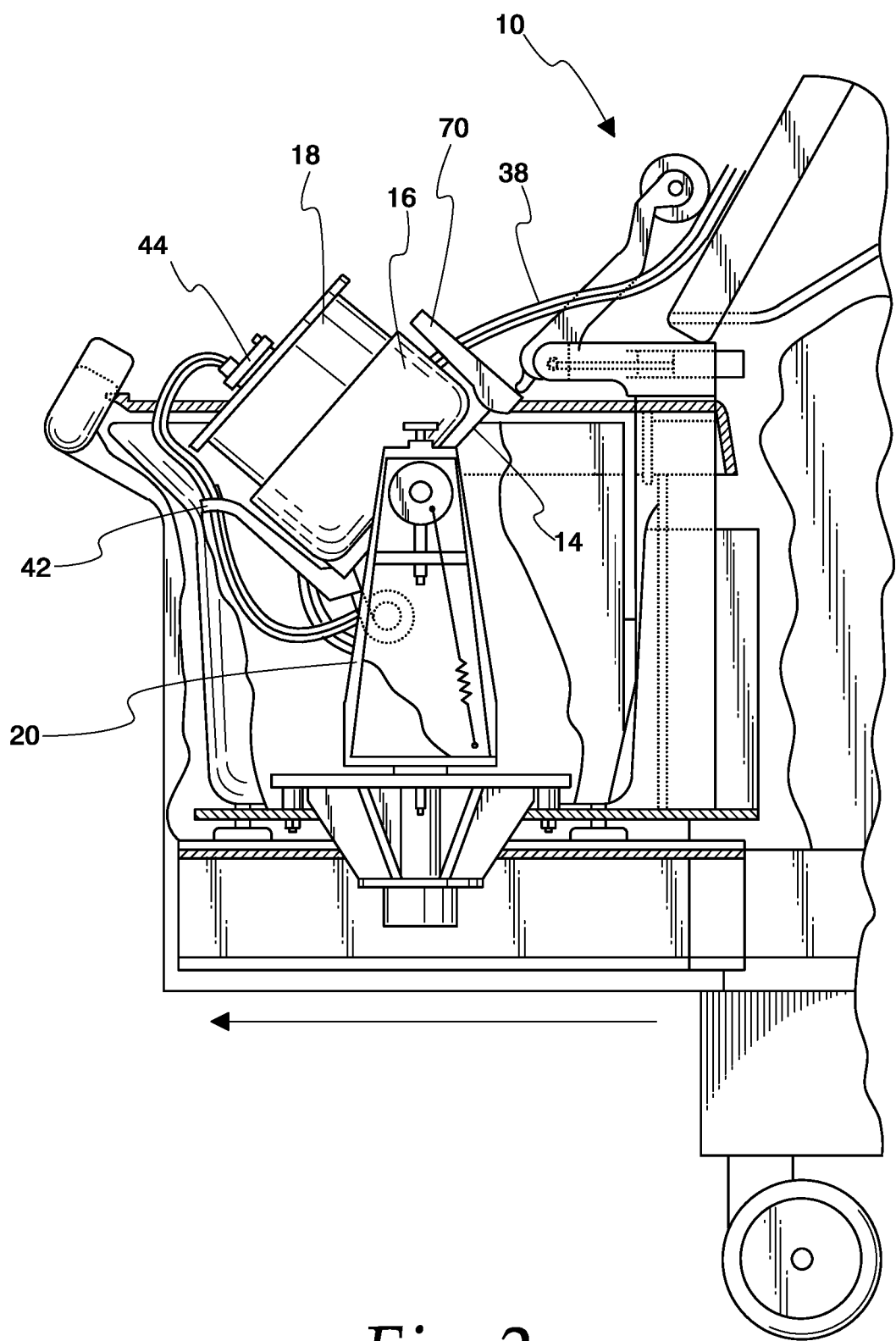
FIG. 2 is a side elevation view, with portions broken away and in section, of the system shown in FIG. 1, with the bowl and spool shown in an upright position for receiving a separation chamber.

FIGS. 1 and 2 show a centrifugal fluid processing system 10 with a system controller including an interface controller 12 (FIG. 11) that may be used in practicing the MNC collection principles of the present disclosure. The system is currently marketed as the AMICUS® separator by Fenwal, Inc. of Lake Zurich, Ill., which is an affiliate of Fresenius Kabi AG of Bad Homburg, Germany, as described in greater detail in U.S. Pat. No. 5,868,696, which is hereby incorporated herein by reference. The system 10 can be used for processing various fluids, but is particularly well suited for processing whole blood, blood components, or other suspensions of biological cellular materials. While MNC collection principles will be described herein with reference to one particular system 10, it should be understood that these principles may be employed with other fluid processing systems without departing from the scope of the present disclosure.

A. The Centrifuge

The fluid processing system 10 includes a centrifuge 14 used to centrifugally separate fluid components. The system 10 may be programmed to separate blood into a variety of components (e.g., platelet-rich plasma and red cells), with various MNC collection procedures, in which the system 10 separates and collects MNCs (e.g., lymphocytes and monocytes) from whole blood, being described herein.

The illustrated centrifuge 14 is of the type shown in U.S. Pat. No. 5,316,667, which is incorporated herein by reference. The centrifuge comprises a bowl 16 and a spool 18. The bowl 16 and spool 18 are pivoted on a yoke 20 between an operating position (FIG. 1) and a loading/unloading position (FIG. 2).

When in the loading/unloading position, the spool 18 can be opened by movement at least partially out of the bowl 16, as FIG. 2 shows. In this position, the operator wraps a flexible separation chamber 22 (see FIG. 3) about the spool 18. Closure of the spool 18 and bowl 16 encloses the chamber 22 for processing. When closed, the spool 18 and bowl 16 are pivoted into the operating position of FIG. 1 for rotation about an axis.

B. The Separation Chamber

Figure 4:
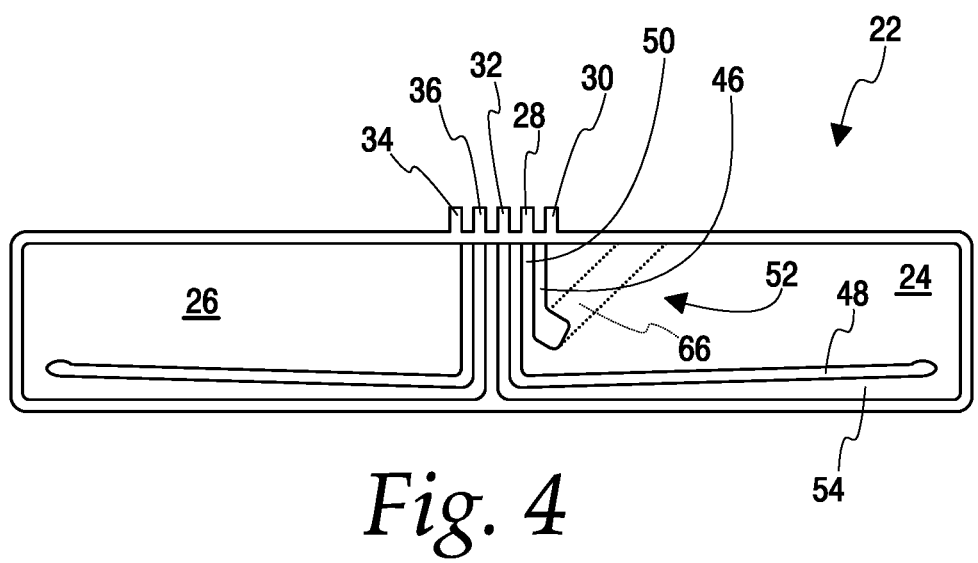
FIG. 4 is a plan view of the separation chamber shown in FIG. 3, out of association with the spool.
Figure 12:
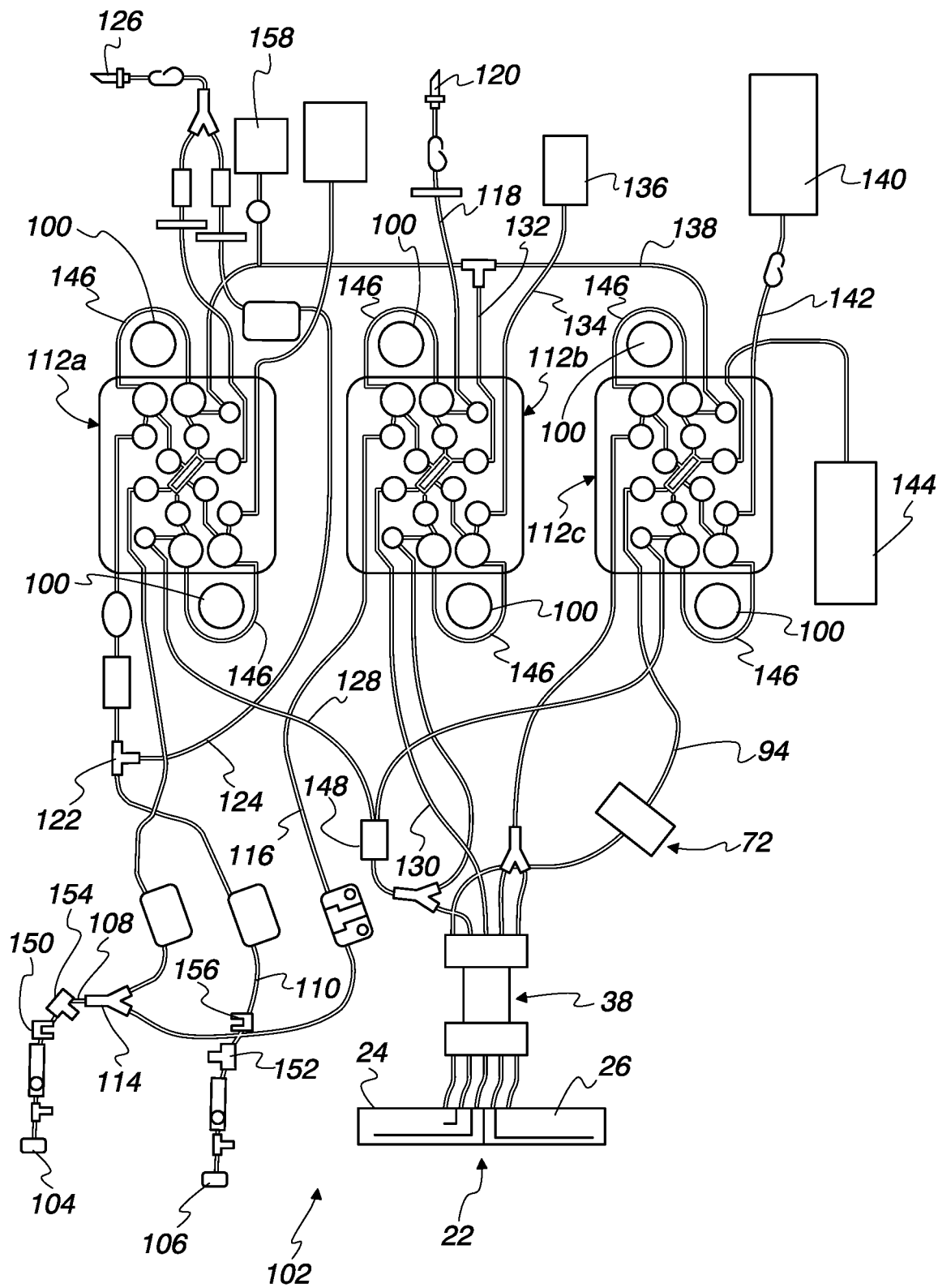
FIG. 12 is a front elevational view of an exemplary disposable fluid processing assembly that may be used in combination with the system of FIGS. 1 and 2 for carrying out blood separation procedures according to the present disclosure.

The separation chamber 22 can be variously constructed. FIG. 4 shows a representative embodiment, while FIG. 12 shows the separation chamber 22 in the context of a disposable fluid processing assembly that is used in combination with the system 10 to define a fluid flow path for blood, separated blood components, and other fluids (e.g., anticoagulant). FIG. 12 illustrates a fluid processing assembly having a "double-needle" configuration in which separate draw and return lines are provided for direct connection to a source for drawing blood into the fluid processing assembly (via the draw line) and returning a separated blood component or some other fluid (e.g., a replacement fluid) to the source (via the return line). The MNC collection techniques described herein may also be practiced using a fluid processing assembly having a "single needle" configuration (as in FIGS. 13 and 14) in which a single access line is directly connected to a source for alternately drawing blood into the fluid processing assembly and returning a separated blood component or some other fluid to the source.

The chamber 22 shown in FIG. 4 allows for either single- or multi-stage processing. When used for multi-stage processing, a first stage 24 separates whole blood into first and second components. Depending on the nature of the separation procedure, one of the components may be transferred into a second stage 26 for further separation. When used for single-stage processing, only the first stage 24 is used for separating blood into its constituents, while the second stage 26 may be filled with saline or the like to balance the chamber 22.

Figure 3:
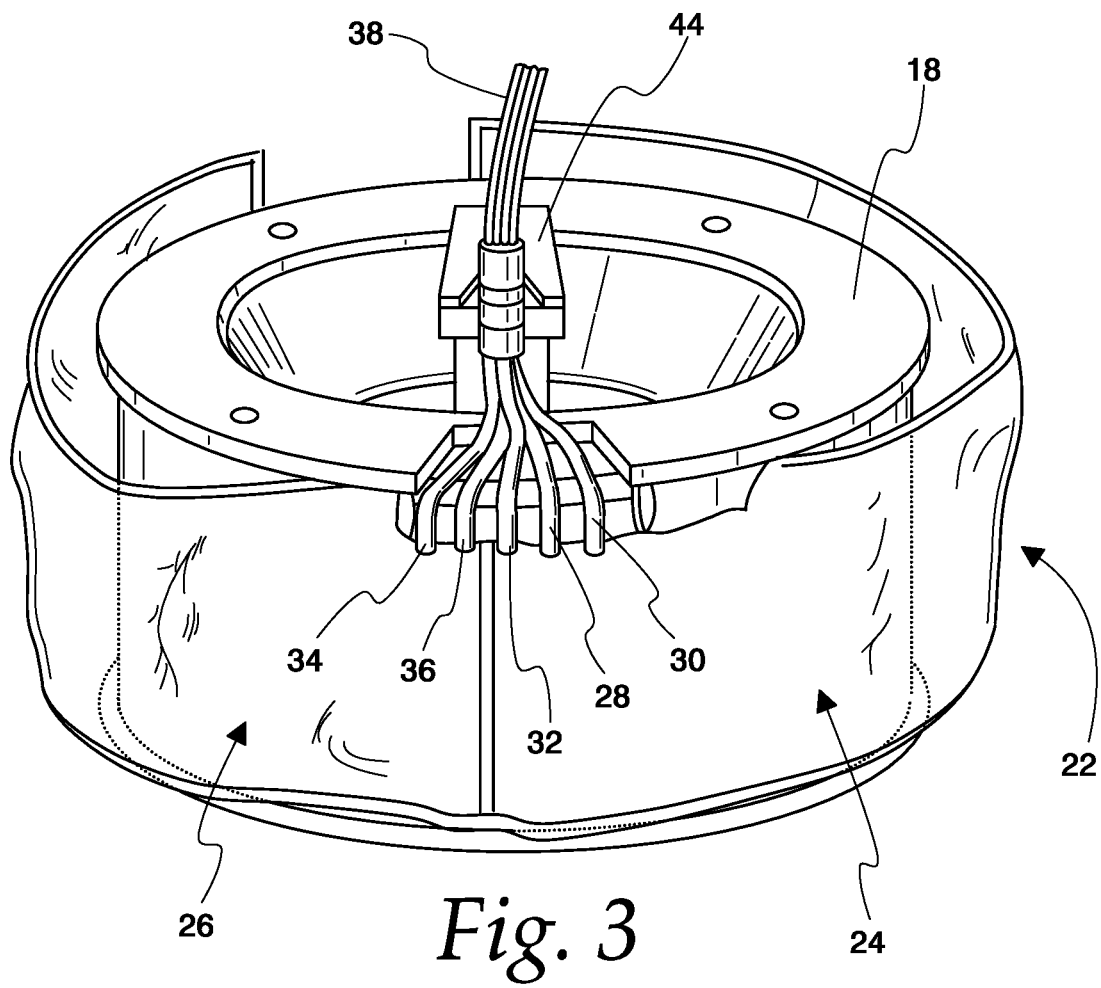
FIG. 3 is a top perspective view of the spool of the centrifuge shown in FIG. 2 in its upright position and carrying the separation chamber.

As FIGS. 3 and 4 best show, there are three ports 28, 30, and 32 associated with the first stage 24. Depending on the particular blood processing procedure, the ports may have different functionality but, in an MNC collection procedure, the port identified at 28 is used for conveying fluids into the first stage 24. During such an MNC collection procedure, the other two ports 30 and 32 serve as outlet ports for separated blood components exiting the first stage 24. More particularly, the first outlet port 30 conveys a low density blood component from the first stage 24, while the second outlet port 32 conveys a high density blood component from the first stage 24.

In a method of carrying out single-stage processing, at least a portion of one or more of the separated components is returned to the fluid source (which may be a living patient or donor or a non-living source, such as a fluid container), while at least a portion of at least one of the other separated components is removed from the first stage 24 and stored. For example, a conventional MNC collection procedure (as described in greater detail in U.S. Pat. No. 5,980,760) begins with a plasma collection phase. During this initial phase, whole blood in the first stage 24 is separated into a plasma constituent (i.e., a low density component, which may include platelets), an interface or buffy coat or MNC-containing layer (i.e., an intermediate density component, which includes MNCs and may also include smaller red blood cells), and packed red blood cells (i.e., a high density component). The plasma constituent and packed red blood cells are removed from the first stage 24 (via the first and second outlet ports 30 and 32, respectively), while the MNC-containing layer builds up in the first stage 24. The plasma constituent is collected, while the packed red blood cells are returned to the blood source.

When a target amount of plasma has been collected, an MNC accumulation phase begins. During this phase, the position of the interface within the first stage 24 is moved closer to the spool 18, such that platelet-rich plasma and packed red blood cells are removed from the first stage 24 (via the first and second outlet ports 30 and 32) while the MNC-containing layer continues to build up in the first stage 24. Portions of the platelet-rich plasma and the packed red blood cells are returned to the blood source, with the remainder of the platelet-rich plasma and packed red blood cells being recirculated through the first stage 24 to maintain a proper hematocrit.

When a target or preselected amount of blood has been processed, the system 10 transitions to a red blood cell collection phase. During this phase, blood separation continues as in the MNC accumulation phase, with recirculation and return of the platelet-rich plasma continuing, while the separated red blood cells are conveyed from the first stage 24 and collected for later use rather than being recirculated or returned to the source.

When a target amount of red blood cells have been collected, the system 10 transitions to an MNC harvest phase. To harvest the MNCs in the MNC-containing layer, the second outlet port 32 is closed to temporarily prevent packed red blood cells from exiting the first stage 24. At least a portion of the collected red blood cells is conveyed into the first stage 24 via the inlet port 28, which forces the MNC-containing layer to exit the first stage 24 via the first outlet port 30 for collection in an MNC collection container as an MNC product.

Following the MNC harvest phase, a plasma flush phase begins. During this phase, collected plasma is used to flush any MNC-containing layer positioned between the separation chamber 22 and the MNC collection container back into the first stage 24. A portion of the collected plasma may be conveyed into the MNC collection container as a storage or suspension medium for the MNC product.

If additional MNC product is to be collected, the various phases may be repeated. Following collection, the MNC product may be treated to further processing, such as extracorporeal photopheresis.

In a different separation procedure, in which multi-stage processing is required, one of the separated blood components will be transferred from the first stage 24 to the second stage 26 via a port 34 associated with the second stage 26. The component transferred to the second stage 26 is further fractionated into sub-components, with one of the sub-components being removed from the second stage 26 via an outlet port 36 and the other sub-component remaining in the second stage 26.

As best shown in FIG. 3, a tubing umbilicus 38 is attached to the ports 28, 30, 32, 34, and 36. The umbilicus 38 interconnects the first and second stages 24 and 26 with each other and with pumps and other stationary components located outside the rotating components of the centrifuge 14 (not shown). As FIG. 1 shows, a non-rotating (zero omega) holder 40 holds the upper portion of the umbilicus 38 in a non-rotating position above the spool 18 and bowl 16. A holder 42 on the yoke 20 rotates the mid-portion of the umbilicus 38 at a first (one omega) speed about the suspended spool 18 and bowl 16. Another holder 44 (FIGS. 2 and 3) rotates the lower end of the umbilicus 38 at a second speed twice the one omega speed (the two omega speed), at which speed the spool 18 and bowl 16 also rotate. This known relative rotation of the umbilicus 38 keeps it untwisted, in this way avoiding the need for rotating seals.

As FIG. 4 shows, a first interior seal 46 is located between the low density outlet port 30 and the inlet port 28. A second interior seal 48 is located between the inlet port 28 and the high density outlet port 32. The interior seals 46 and 48 form a fluid passage 50 (an inlet for whole blood or the like) and a low density collection region 52 in the first stage 24. The second seal 48 also forms a fluid passage 54 (a high density blood component outlet in an MNC collection procedure) in the first stage 24.

In an MNC collection procedure, the fluid passage 50 channels blood directly into the circumferential flow path immediately next to the low density collection region 52. As shown in FIG. 5, the blood separates into an optically dense layer 56 containing cellular components, which forms as cellular components move under the influence of centrifugal force toward the high-G (outer) wall 62. The optically dense layer 56 will include red blood cells (and, hence, will be referred to herein as the "RBC layer") but, depending on the speed at which the centrifuge 14 is spun, other cellular components (e.g., larger white blood cells and platelets) may also be present in the RBC layer 56.

The movement of the component(s) of the RBC layer 56 displaces less dense blood components radially toward the low-G (inner) wall 64, forming a second, less optically dense layer 58. The less optically dense layer 58 includes plasma (and, hence, will be referred to herein as the "plasma layer or plasma constituent") but, depending on the speed at which the centrifuge 14 is rotated and the length of time that the blood is resident in the centrifuge, other components (e.g., smaller platelets) may also be present in the plasma layer 58.

The transition between the RBC layer 56 and the plasma layer 58 is generally referred to as the interface or buffy coat or MNC-containing layer 60, as described above and shown in FIG. 5. Platelets and white blood cells (including MNCs) typically occupy this transition region.

The location of the interface 60 within the chamber 22 can dynamically shift during blood processing, as FIGS. 6 and 7 show. If the location of the interface 60 is too high (that is, if it is too close to the low-G wall 64 and the removal port 30, as FIG. 6 shows), red blood cells can spill over and into the low density collection region 52, adversely affecting the quality of the plasma constituent 58. On the other hand, if the location of the interface 60 is too low (that is, if it resides too far away from the low-G wall 64, as FIG. 7 shows), the collection efficiency of the system 10 may be impaired.

As FIG. 5 shows, a ramp 66 extends from the high-G wall 62 of the bowl 16 at an angle across the low density collection region 52. The angle, measured with respect to the axis of the first outlet port 30 is about 30° in one embodiment. FIG. 5 shows the orientation of the ramp 66 when viewed from the low-G wall 64 of the spool 18. FIG. 4 shows, in phantom lines, the orientation of the ramp 66 when viewed from the high-G wall 62 of the bowl 16.

Further details of the angled relationship of the ramp 66 and the first outlet port 30 can be found in U.S. Pat. No. 5,632,893, which is incorporated herein by reference.

The ramp 66 forms a tapered wedge that restricts the flow of fluid toward the first outlet port 30. The top edge of the ramp 66 extends to form a constricted passage 68 along the low-G wall 64. The plasma layer 58 must flow through the constricted passage 68 to reach the first outlet port 30.

As FIG. 5 shows, the ramp 66 makes the interface 60 between the RBC layer 56 and the plasma layer 58 more discernible for detection, displaying the RBC layer 56, plasma layer 58, and interface 60 for viewing through the high-G wall 62 of the chamber 22.

Further details of the separation chamber 22 and its operation may be found in U.S. Pat. No. 5,316,667.

C. The Interface Controller

The interface controller 12 (FIG. 11) includes a viewing head or interface optical sensor assembly 70 carried on the yoke 20 (see FIGS. 1 and 8) and an outlet optical sensor assembly 72 which is associated with tubing connected to the first outlet port 30. Alternatively, rather than being carried on the yoke 20, the interface optical sensor assembly 70 may be mounted to a radial location of the centrifuge bucket or enclosure, as described in U.S. Patent Application Publication Nos. 2014/0057771 and 2015/0219558, both of which are incorporated herein by reference. The interface optical sensor assembly 70 is oriented to optically view the transition in optical density between the RBC layer 56 and the plasma layer 58 on the ramp 66. The outlet optical sensor assembly 72 monitors the optical density of fluid exiting the first stage 24 via the first outlet port 30.

The interface controller 12 is functional to determine the location of the interface 60 on the ramp 66 and, if the interface 60 is located at an improper location (e.g., in the locations of FIG. 6 or 7), to correct the location of the interface 60.

(1) The Interface Optical Sensor Assembly

Referring to FIGS. 8-10, the interface optical sensor assembly 70, carried by the yoke 20 or mounted to a stationary radial location of the centrifuge bucket or enclosure, includes a light source 74, which emits light that is absorbed by red blood cells. In the illustrated embodiment, the light source 74 includes a circular array of red light emitting diodes 76, but other wavelengths absorbed by red blood cells, like green or infrared, could also be used.

In the illustrated embodiment, seven light emitting diodes 76 comprise the light source 74. More diodes 76 may be used, or fewer diodes 76 can be used, depending upon the optical characteristics desired. Further, non-LED lights may also be employed without departing from the scope of the present disclosure.

The interface optical sensor assembly 70 also includes a light detector 78 (FIGS. 9 and 10), which is mounted adjacent to the light source 74. In one embodiment, the light detector 78 comprises a PIN diode detector, which is located generally in the geometric center of the circular array of light emitting diodes 76. Other types of light detectors may also be employed.

If mounted to the yoke 20, the yoke 20 and the interface optical sensor assembly 70 rotate at a one omega speed, as the spool 18 and bowl 16 rotate at an average speed of two omega. If mounted to a stationary portion of the centrifuge bucket or enclosure, the interface optical sensor assembly 70 remains stationary while the yoke 20 rotates at a one omega speed and the spool 18 and bowl 16 rotate at an average speed of two omega. The light source 74 directs light onto the rotating bowl 16. In the illustrated embodiment, the bowl 16 is transparent to the light emitted by the source 74 only in the region 80 where the bowl 16 overlies the interface ramp 66 (FIG. 8). In the illustrated embodiment, the region 80 comprises a window cut out in the bowl 16. The remainder of the bowl 16 that lies in the path of the interface optical sensor assembly 70 comprises an opaque or light absorbing material.

The interface ramp 66 is made of a light transmissive material. The light from the source 74 will thereby pass through the transparent region 80 of the bowl 16 and the ramp 66 every time the rotating bowl 16 and interface optical sensor assembly 70 align. The spool 18 may also carry a light reflective material 82 (FIGS. 9 and 10) behind the interface ramp 66 to enhance its reflective properties. The spool 18 reflects incoming light received from the source 74 out through the transparent region 80 of the bowl 16, where it is sensed by the detector 78. In the illustrated embodiment, light passing outward from the source 74 and inward toward the detector 78 passes through a focusing lens 84 (shown in FIGS. 9 and 10), which forms a part of the viewing head 70.

Such an arrangement optically differentiates the reflective properties of the interface ramp 66 from the remainder of the bowl 16. This objective can be achieved in other ways. For example, the light source 74 could be gated on and off with the arrival and passage of the ramp 66 relative to its line of sight. As another example, the bowl 16 outside the transparent region 80 could carry a material that reflects light, but at a different intensity than the reflective material 82 behind the interface ramp 66.

As the transparent interface region 80 of the bowl 16 comes into alignment with the interface optical sensor assembly 70, the detector 78 will first sense light reflected through the plasma layer 58 on the ramp 66. Eventually, the RBC layer 56 adjacent the interface 60 on the ramp 66 will enter the optical path of the interface optical sensor assembly 70. The RBC layer 56 absorbs light from the source 74 and thereby reduces the previously sensed intensity of the reflected light. The length of time that the higher intensity of reflected light is sensed by the detector 78 represents the amount of light from the source 74 that is not absorbed by the RBC layer 56 adjacent to the interface 60. With this information, a processing element or module 86 (FIG. 11) can determine the location of the interface 60 on the ramp 66 relative to the constricted passage 68. A more detailed discussion of the algorithms by which the interface controller 12 receives and processes signals to determine the location of the interface 60 on the ramp 66 may be found in U.S. Pat. No. 6,312,607, which is incorporated herein by reference.

Figure 11:
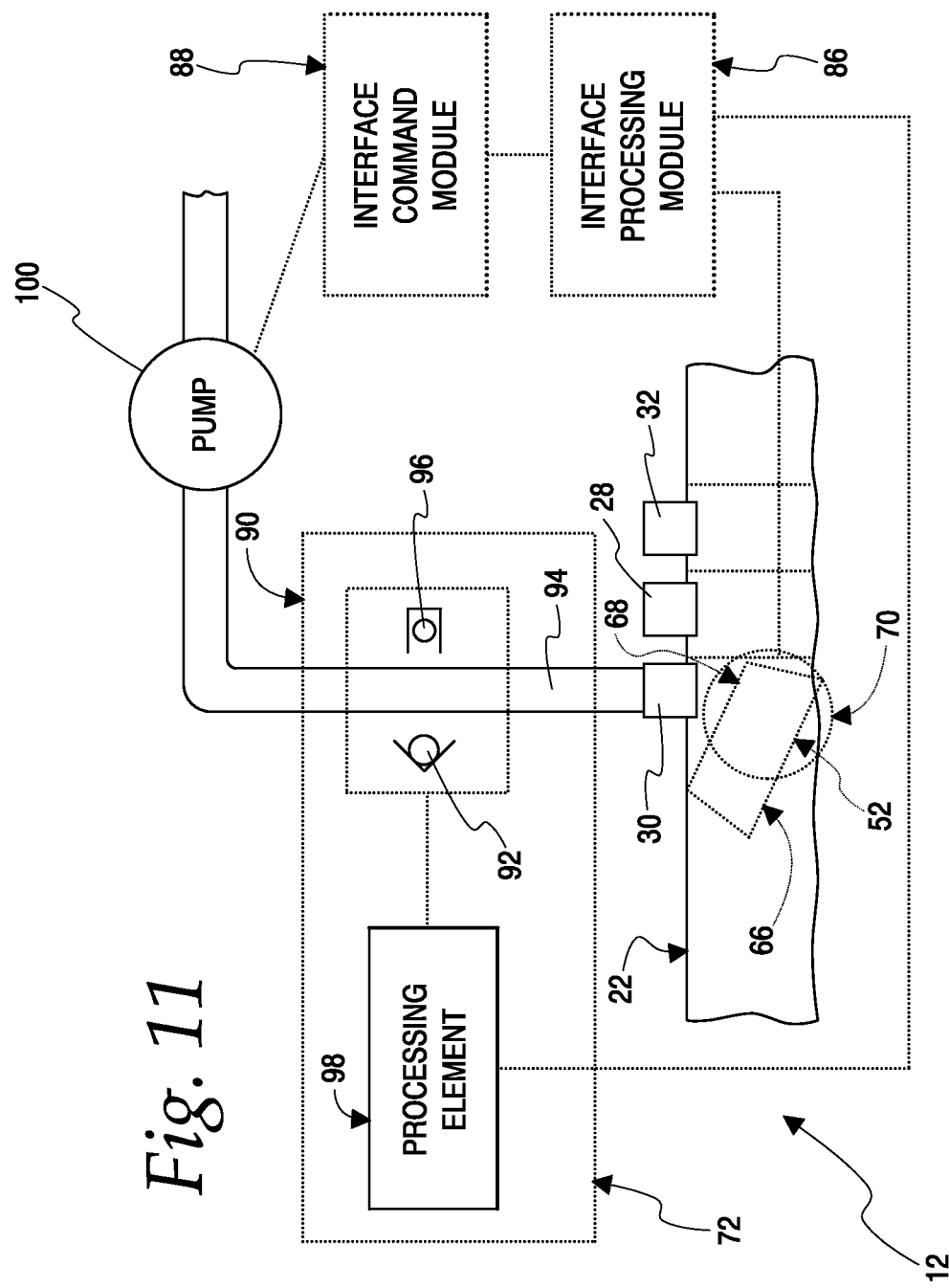
FIG. 11 is a schematic view of a blood calibration element, which forms a part of the interface controller.

When the location of the interface 60 on the ramp 66 has been determined, the processing element 86 outputs that information to an interface command element or module 88 (FIG. 11). The command element 88 includes a comparator, which compares the interface location output with a desired interface location to generate an error signal. The error signal may take a number of forms but, in one embodiment, is expressed in terms of a targeted red blood cell percentage value (i.e., the percentage of the ramp 66 which should be occupied by the RBC layer 56).

When the control value is expressed in terms of a targeted red blood cell percentage value, a positive error signal indicates that the RBC layer 56 on the ramp 66 is too small (as FIG. 7 shows). The interface command element 88 generates a signal to adjust an operational parameter accordingly, such as by increasing the rate at which plasma is removed through the first outlet port 30 under action of a pump 100 (FIG. 11). The interface 60 moves toward the constricted passage 68 to the desired control position (as FIG. 5 shows), where the error signal is zero.

A negative error signal indicates that the RBC layer 56 on the ramp 66 is too large (as FIG. 6 shows). The interface command element 88 generates a signal to adjust an operational parameter accordingly, such as by decreasing the rate at which plasma is removed through the first outlet port 30. The interface 60 moves away from the constricted passage 68 to the desired control position (FIG. 5), where the error signal is again zero.

(2) The Outlet Optical Sensor Assembly

The interface controller 12 further includes an outlet optical sensor assembly 72 (FIG. 11), which is configured to monitor the optical density of plasma outside of the separation chamber 22. The outlet optical sensor assembly 72 may be positioned anywhere in the fluid circuit outside of the blood separation chamber 22 where separated plasma is present but, in the illustrated embodiment is associated with tubing 94 connected to the first outlet port 30 so as to monitor plasma exiting the first stage 24 (or any other fluid exiting the first stage 24 via the first outlet port 30). The outlet optical sensor assembly 72 compares the optical density of separated plasma to a baseline fluid (e.g., saline) exiting the first outlet port 30. If the optical density of the plasma is significantly different from saline (i.e., if the plasma has a reduced clarity), then it may be indicative of conditions of lipemia, hemolysis, or hyperbilirubinemia. The outlet optical sensor assembly 72 may also detect a change in the nature of the fluid exiting the first outlet port 30, such as when the fluid transitions from plasma to the MNC-containing layer during the MNC harvest phase of an MNC collection procedure.

The outlet optical sensor assembly 72 includes an optical monitor 90 (see FIG. 11), which senses the optical density of fluid exiting the first outlet port 30 or (in the case of a multi-stage separation procedure) entering the second stage inlet port 34. In one embodiment, the optical monitor 90 is a conventional hemoglobin detector of the type used on the Autopheresis-C® blood processing device sold by Fenwal, Inc. The optical monitor 90 comprises a red light-emitting diode 92, which emits light into the outlet tubing 94 connected to the first outlet port 30 on the outside of the blood separation chamber 22. The optical monitor 90 further includes a PIN diode detector 96 on the opposite side of the tubing 94.

Different or additional light sources could also be used without departing from the scope of the present disclosure. For example, it may be advantageous to include separate red and green light-emitting diodes to distinguish between lipemic and hemolytic conditions in the whole blood and/or plasma layer 58. If, when considering plasma in the tubing 94, the overall transmissivity of the plasma is below a certain level (indicating that the plasma is relatively turbid and may be either lipemic or hemolytic), the red and green transmissions are separately considered. If the red and green transmissions decrease by a similar percentage (from the level of transmission through saline), then it is indicative of lipemia (because green and red light are absorbed to a similar extent by lipids). However, if the green transmission decreases to a much greater degree than the red transmission, it is indicative of hemolytic plasma (because green light is more readily absorbed by hemoglobin than red light).

The outlet optical sensor assembly 72 also includes a processing element 98, which receives signals from the monitor 90 to compute the optical transmission of the liquid conveyed through the tubing 94 by operation of a pump 100 of the fluid processing system 10. A more detailed discussion of a set of exemplary algorithms by which the optical densities of the tubing 94 itself, saline present in the tubing 94, and other fluid in the outlet tubing 94 may be determined can be found in U.S. Pat. No. 6,312,607.

D. Alternative MNC Collection Procedures

According to one approach, the conventional MNC collection procedure is replaced with a modified procedure. In general, such modified procedures increase the volume of red blood cells in the fluid processing assembly earlier in the procedure than in the conventional approach, which is advantageous if the procedure is terminated early because it ensures that a sufficient volume of red blood cells will be available for MNC collection.

Such modified procedures may require a greater volume of extracorporeal blood and/or a higher hematocrit than is required in a conventional procedure. Therefore, prior to beginning an MNC collection procedure, the system controller may ascertain whether the blood source can tolerate an alternative MNC collection procedure of the type described herein. If it is determined that an alternative MNC collection procedure is practicable (i.e., if the blood source has at least a minimum total blood volume and/or a minimum hematocrit), then the conventional MNC collection procedure may be replaced by one of the alternative MNC collection procedures described herein. Notably, the alternative MNC collection procedures described herein may be practiced using the same fluid processing system 10 and fluid processing assembly that are used for the conventional MNC collection procedure. Accordingly, an operator or technician does not need to know which MNC collection procedure will be executed when mounting a fluid processing assembly to the fluid processing system 10.

(1) Early Red Blood Cell Collection

According to one alternative MNC collection procedure, the conventional MNC collection procedure is modified by executing the red blood cell collection phase before the MNC accumulation phase. Thus, the modified MNC collection procedure begins with a plasma collection phase, as in the conventional MNC collection procedure. During this initial phase, whole blood in the first stage 24 of the separation chamber 22 is separated into platelet-poor plasma, the MNC-containing layer, and red blood cells. The platelet-poor plasma and red blood cells are removed from the first stage 24 (via the first and second outlet ports 30 and 32, respectively), while the MNC-containing layer builds up in the first stage 24. The platelet-poor plasma is collected, while the red blood cells are returned to the blood source.

When a target amount of plasma has been collected, the system 10 transitions to a red blood cell collection phase, rather than an MNC accumulation phase (which is the second phase in a conventional MNC collection procedure). During this phase, the position of the interface within the first stage 24 is moved closer to the low-G wall 64, such that platelet-rich plasma and packed red blood cells are removed from the first stage 24 (via the first and second outlet ports 30 and 32, respectively) while the MNC-containing layer continues to build up in the first stage 24. At least a portion of the platelet-rich plasma is recirculated through the separation chamber 22, while another portion of the platelet-rich plasma may be returned to the blood source. The separated red blood cells are conveyed from the first stage 24 and collected for later use.

When a target amount of red blood cells has been collected, the system 10 transitions to an MNC accumulation phase. During this phase, blood separation continues as in the red blood cell collection phase, with blood in the separation chamber 22 being separated into a plasma constituent, MNC-containing layer, and packed red blood cells. Portions of the plasma constituent and the packed red blood cells are returned to the blood source, with the remainder of the platelet-rich plasma and packed red blood cells being recirculated through the first stage 24 to maintain a proper hematocrit.

When a target or preselected amount of blood has been processed, the system 10 transitions to an MNC harvest phase. To harvest the MNCs in the MNC-containing layer, the second outlet port 32 is closed to temporarily prevent packed red blood cells from exiting the first stage 24. At least a portion of the collected red blood cells is conveyed into the first stage 24 via the inlet port 28, which forces the MNC-containing layer to exit the first stage 24 via the first outlet port 30 for collection in an MNC collection container as an MNC product.

Following the MNC harvest phase, a plasma flush phase begins. During this phase, collected plasma is used to flush any MNC-containing layer positioned between the separation chamber 22 and the MNC collection container back into the first stage 24. A portion of the collected plasma may be conveyed into the MNC collection container as a storage or suspension medium for the MNC product.

If additional MNC product is to be collected, the various phases may be repeated. Following collection, the MNC product may be treated to further processing, such as extracorporeal photopheresis.

(2) Early Blood Collection

According to another alternative MNC collection procedure, the conventional MNC collection procedure is modified by adding a blood collection phase. The blood collection phase may either be a new first phase or may represent a modification to the plasma collection phase that begins a conventional MNC collection procedure.

If the MNC collection procedure is to begin with a blood collection phase, blood is drawn into the fluid processing assembly and directed to the red blood collection container rather than to the separation chamber 22. The amount of blood collected in the red blood cell collection container may be based on the amount of red blood cells required to convey MNCs from the separation chamber 22 to the MNC collection container later in the procedure. For example, the amount of blood collected may be selected to include all of the required red blood cells, or a lesser amount may instead be collected.

Following the blood collection phase, the system 10 transitions to a plasma collection phase. During this phase, blood begins to flow into the first stage 24 of the separation chamber 22, rather than flowing into the red blood cell collection container. The blood in the first stage 24 is separated into platelet-poor plasma, the MNC-containing layer, and red blood cells. The platelet-poor plasma and red blood cells are removed from the first stage 24 (via the first and second outlet ports 30 and 32, respectively), while the MNC-containing layer builds up in the first stage 24. The platelet-poor plasma is collected, while the red blood cells are returned to the blood source.

Alternatively, rather than beginning with a dedicated blood collection phase, the MNC collection procedure may instead begin with a modified plasma collection phase. During such a modified plasma collection phase, a first portion of blood is conveyed into the red blood cell collection container while a second portion of the blood is simultaneously conveyed into the first stage 24 of the separation chamber 22. The blood in the first stage 24 is separated, with platelet-poor plasma being conveyed out of the separation chamber 22 for collection and red blood cells being returned to the blood source, as in the plasma collection phase of the conventional MNC collection procedure. The percentages of blood being conveyed to the red blood cell collection and to the separation chamber 22 may be selected such that a suitable amount of blood is collected at the same time that a target amount of plasma has been collected. Alternatively, if blood collection is or would be completed prior to plasma collection or if plasma collection is or would be completed prior to blood collection, the percentages may be varied during this phase to complete both objectives (e.g., directing more or all drawn blood into the red blood cell collection container to complete blood collection or directing more or all drawn blood into the separation chamber 22 to complete plasma collection).

Once target amounts of blood and plasma have been collected, an MNC accumulation phase begins. During this phase, the position of the interface within the first stage 24 is moved closer to the low-G wall 64, such that platelet-rich plasma and packed red blood cells are removed from the first stage 24 (via the first and second outlet ports 30 and 32, respectively) while the MNC-containing layer continues to build up in the first stage 24. Portions of the platelet-rich plasma and the packed red blood cells are returned to the blood source, with the remainder of the platelet-rich plasma and packed red blood cells being recirculated through the first stage 24 to maintain a proper hematocrit.

When a target or preselected amount of blood has been processed, the system 10 transitions to a red blood cell collection phase. During this phase, blood separation continues as in the MNC accumulation phase, with recirculation and return of the platelet-rich plasma continuing, while the separated red blood cells are conveyed from the first stage 24 and collected for later use rather than being recirculated or returned to the source. Rather than blood being drawn into the separation chamber 22 exclusively from the blood source, at least a portion of the blood entering the separation chamber 22 during this phase comes from the red blood cell collection container. If enough blood has been collected, then all of the blood conveyed into the separation chamber 22 may come from the red blood cell collection container. Alternatively, if a lesser amount of blood has been collected, then all of the blood from the red blood cell collection container may be conveyed into the separation chamber 22, with an amount of blood from the blood source also being conveyed into the separation chamber 22.

When a target amount of red blood cells have been collected, the system 10 transitions to an MNC harvest phase. To harvest the MNCs in the MNC-containing layer, the second outlet port 32 is closed to temporarily prevent packed red blood cells from exiting the first stage 24. At least a portion of the collected red blood cells is conveyed into the first stage 24 via the inlet port 28, which forces the MNC-containing layer to exit the first stage 24 via the first outlet port 30 for collection in an MNC collection container as an MNC product.

Following the MNC harvest phase, a plasma flush phase begins. During this phase, collected plasma is used to flush any MNC-containing layer positioned between the separation chamber 22 and the MNC collection container back into the first stage 24. A portion of the collected plasma may be conveyed into the MNC collection container as a storage or suspension medium for the MNC product.

If additional MNC product is to be collected, the various phases may be repeated. Following collection, the MNC product may be treated to further processing, such as extracorporeal photopheresis.

E. Mid-Procedure Termination Recovery Techniques

As described above, a modified MNC collection procedure may be advantageous to minimize the impact of mid-procedure termination. However, if the blood source cannot tolerate a modified MNC collection procedure of the type described herein, then a conventional MNC collection procedure must be carried out. In this case, the controller of the system 10 may be programmed with techniques that allow for at least partial MNC collection in the event that the procedure is terminated before the red blood cell collection phase is completed. Such techniques may involve salvaging red blood cells or red blood cell-containing from within the fluid processing assembly to collect all or a portion of the red blood cells required to harvest the MNCs. Alternatively, under certain circumstances, the fluid processing assembly may be converted to a different configuration for continued processing and MNC collection.

(1) Blood Salvage To Red Blood Cell Collection Container

FIG. 12 shows a fluid processing assembly 102 that may be used in carrying out the MNC collection procedures and techniques described herein. The illustrated fluid processing assembly 102 has a "two needle" configuration, which includes a pair of fluid source access devices 104 and 106 (e.g., phlebotomy needles) configured for direct connection to a fluid source. The fluid source access devices 104 and 106 are connected by tubing 108 and 110 (referred to herein as a draw line and a return line, respectively) to a first or left cassette 112a. One of the fluid source access devices 104 is used to draw fluid (e.g., blood in an MNC collection procedure) from the fluid source into the fluid processing assembly 102 and is connected to the left cassette 112a through a y-connector 114. The other leg of the y-connector 114 is connected to tubing 116 which leads to a second or middle cassette 112b. The tubing 116 is connected, through the middle cassette 112b, to additional tubing 118, which includes a container access device 120 (e.g., a sharpened cannula or spike connector) for accessing the interior of a container, which may be an anticoagulant container in the case of a blood treatment operation. During a blood treatment operation (e.g., an MNC collection procedure), anticoagulant from the anticoagulant container is added to the blood from the fluid source at the y-connector 114 prior to entering the left cassette 112a.

The other fluid source access device 106 is used to deliver or return the original drawn fluid, a component of that fluid, and/or some other fluid to the fluid source and is also connected to the left cassette 112a through a y-connector 122. The other leg of the y-connector 122 is connected to tubing 124 in fluid communication at its other end with a container access device 126. Although not illustrated, the container access device 126 may be associated with a container having an amount of fluid (e.g., saline) to be used to prime the fluid processing assembly 102 and/or delivered to the fluid source via the fluid source access device 106.

The left cassette 112a is also connected to tubing 128 in fluid communication with the separation chamber 22, which separates the fluid into its constituent parts and returns the fluid components to the fluid processing assembly 102, as described above. One of the fluid components (which may be separated red blood cells in an MNC collection procedure) is conveyed to the middle cassette 112b from the separation chamber 22 via tubing 130, while another separated component (which may be a plasma constituent in an MNC collection procedure) is conveyed to a third or right cassette 112c of the fluid processing assembly 102 from the separation chamber 22 via tubing 94. The first separated component (e.g., red blood cells) may be pumped to the left cassette 112a via tubing 132, where it is returned to the fluid source, or may instead exit the middle cassette 112b via tubing 134 to a collection container 136 (referred to as a red blood cell collection container, in the context of a blood separation procedure) for storage or later use or may be recirculated from the middle cassette 112b through the separation chamber 22, as described above. The second separated component (e.g., the plasma constituent) may be pumped back to the left cassette 112a via tubing 138 for return to the fluid source and/or it may be pumped into a collection container 140 (referred to as a plasma collection container, in the context of a blood separation procedure) via different tubing 142 or recirculated from the right cassette 112c through the separation chamber 22, as described above. The destination of the various fluids passing through the cassettes depends upon the actuation of the various valves of the cassettes, as described in greater detail in U.S. Pat. No. 5,462,416, which is incorporated herein by reference.

Each illustrated cassette 112 includes an injection-molded body that is compartmentalized by an interior wall to present or form a topside (which faces away from the fluid processing system 10, during use) and an underside (which faces toward the fluid processing system 10, during use). A flexible diaphragm overlies and peripherally seals the underside of each cassette 112, while a generally rigid upper panel overlies the topside of each cassette 112 and is sealed peripherally and to raised, channel-defining walls in the cassette 112.

The top- and undersides of the cassettes 112 contain preformed cavities. On the underside of the cassettes 112, the cavities form an array of valve stations and an array of pressure sensing stations. On the topside of the cassettes 112, the cavities form an array of channels or paths for conveying fluids. The valve stations communicate with the flow paths through the interior wall to interconnect them in a predetermined manner. The sensing stations also communicate with the flow paths through the interior wall to sense pressures in selected regions. The number and arrangement of the flow paths, the valve stations, and the sensing stations can vary without departing from the scope of the present disclosure.

In the illustrated embodiment, ten pre-molded tube connectors extend out along opposite side edges of each cassette 112. The tube connectors are arranged five on one side edge and five on the other side edge. The other side edges of the cassettes 112, as illustrated, are free of tube connectors. The tube connectors are associated with external tubing to associate the cassettes 112 with the remainder of the fluid processing assembly (e.g., to a plasma collection container 140, an MNC collection container 144, or a red blood cell collection container 136) or to define tubing loops 146 that interact with pumps 100 of the fluid processing system 10 to flow fluid through the flow processing assembly 102, as described in greater detail in U.S. Pat. No. 5,462,416.

The tube connectors communicate with various interior flow paths, which constitute the flow paths of the cassettes 112 through which a fluid enters or exits the cassette 112. The remaining interior flow paths of the cassette 112 constitute branch paths that link the flow paths associated with the tube connectors to each other through the valve stations and sensing stations. The particular configuration of one suitable cassette is described in greater detail in U.S. Pat. No. 5,462,416.

The fluid processing assembly 102 may also include a number of other components, including clamps or valves and a drip chamber 148 that fluid passes through before entering the separation chamber 22. The draw and return lines 108 and 110 are illustrated with pairs of connectors for converting the fluid processing assembly 102 from the "double needle" configuration of FIG. 12 to one of the "single needle" configurations of FIGS. 13 and 14, as will be described in greater detail herein.

Depending on the current phase when an MNC collection procedure is terminated, blood drawn into the fluid processing assembly 102 may be positioned between the draw line 108 and the separation chamber 22. In particular, the blood may be positioned within the left cassette 112a, the drip chamber 148, and in associated tubing. In this case, the controller of the fluid processing system 10 may actuate various pumps and valves to direct the blood in the left cassette 112a and/or the drip chamber 148 to the red blood cell collection container 136 instead of to its original destination (i.e., the separation chamber 22). The controller may then advance the procedure to the next appropriate phase, with the blood in the red blood cell collection container 136 (and, optionally, separated red blood cells previously conveyed into the red blood cell collection container 136) being conveyed into the separation chamber 22.

If the procedure is terminated during an earlier phase (namely, before the red blood cell collection phase), the salvaged blood from the red blood cell collection container 136 may be separated to accumulate additional MNCs in the separation chamber 22, with red blood cells separated from the blood being collected for later harvesting MNCs. If the procedure is terminated later (i.e., during the red blood cell collection phase), then red blood cells separated from the salvaged blood (along with any separated red blood cells already present in the red blood cell collection container 136) may be used to collect MNCs as part of a modified MNC harvest phase.

(2) Blood And Red Blood Cell Salvage To Separation Chamber

According to a variation of the preceding recovery protocol, the controller of the fluid processing system 10 may instead actuate various pumps and valves to convey blood in the fluid processing assembly 102 (e.g., in the left cassette 112a or in the drip chamber 148) directly into the separation chamber 22 immediately following mid-procedure termination, rather than first directing it to the red blood cell collection container 136. The controller may additionally or alternatively (depending on the current phase when the MNC collection procedure is terminated) actuate various pumps and valves to convey separated red blood cells in the left and/or middle cassettes 112a and 112b into the separation chamber 22. As necessary, the controller may actuate various pumps and valves to draw saline into the fluid processing assembly 102 from a saline container (not illustrated) to convey the blood and/or separated red blood cells to the separation chamber 22.

When the blood and/or red blood cells have been conveyed into the separation chamber 22, the controller may then advance the procedure to the next appropriate phase. If the procedure is terminated during an earlier phase (namely, before the red blood cell collection phase), any salvaged blood may be separated to accumulate additional MNCs in the separation chamber 22, with red blood cells separated from the blood being collected for later harvesting MNCs. If the procedure is terminated later (i.e., during the red blood cell collection phase), then any salvaged red blood cells and/or red blood cells separated from the salvaged blood (along with any separated red blood cells already present in the red blood cell collection container 136) may be used to collect MNCs as part of a modified MNC harvest phase.

This and the preceding recovery protocol may both be programmed into a controller, with the controller selecting one of the protocols depending on any of a variety of factors, such as the nature of the disruption leading to process termination and the current phase at the time of termination.

(3) Fluid Processing Assembly Conversion

Figure 13:
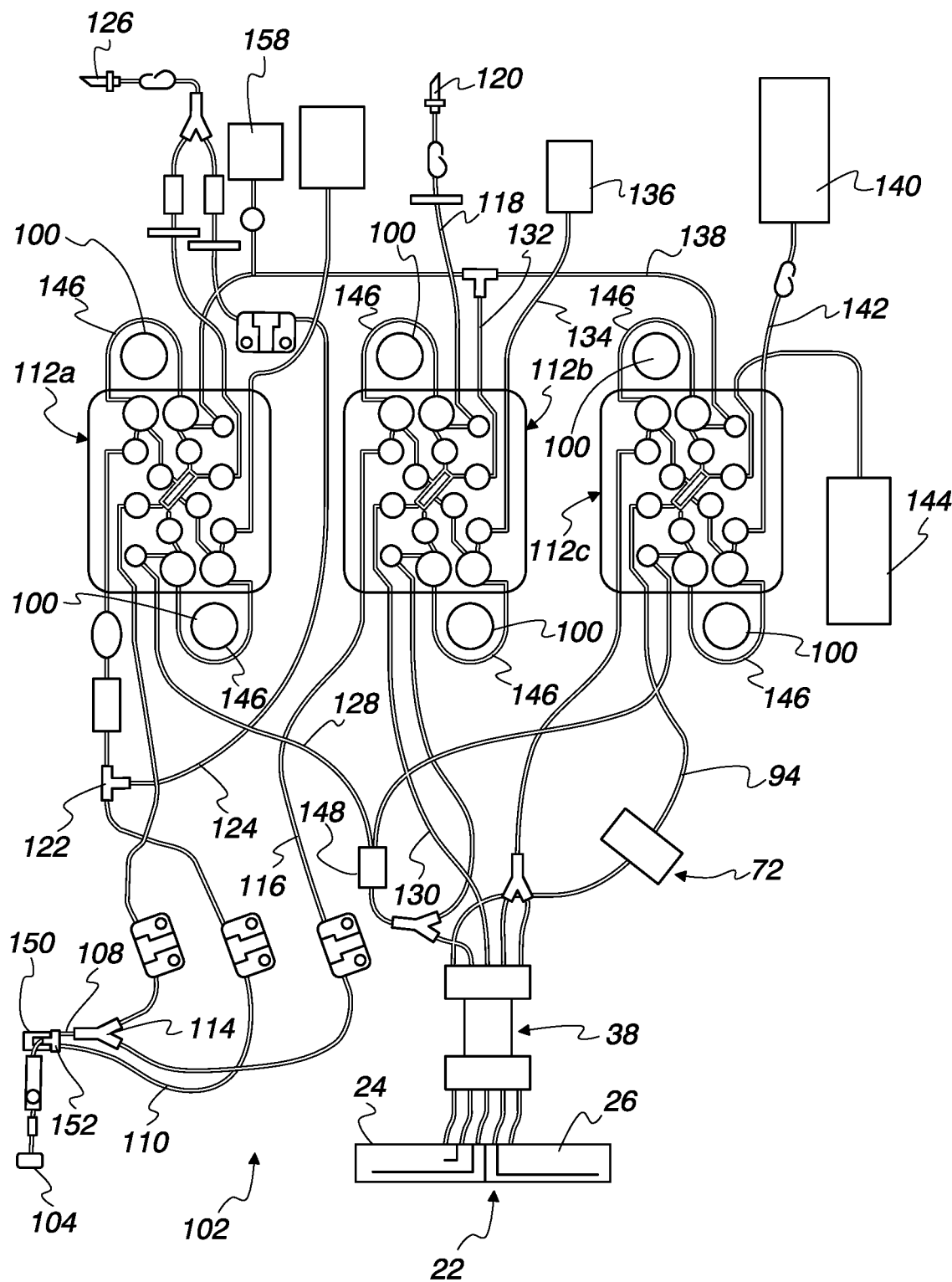
FIG. 13 illustrates the fluid processing assembly of FIG. 12, converted from the "double needle" configuration of FIG. 12 to a "single needle" configuration.
Figure 14:
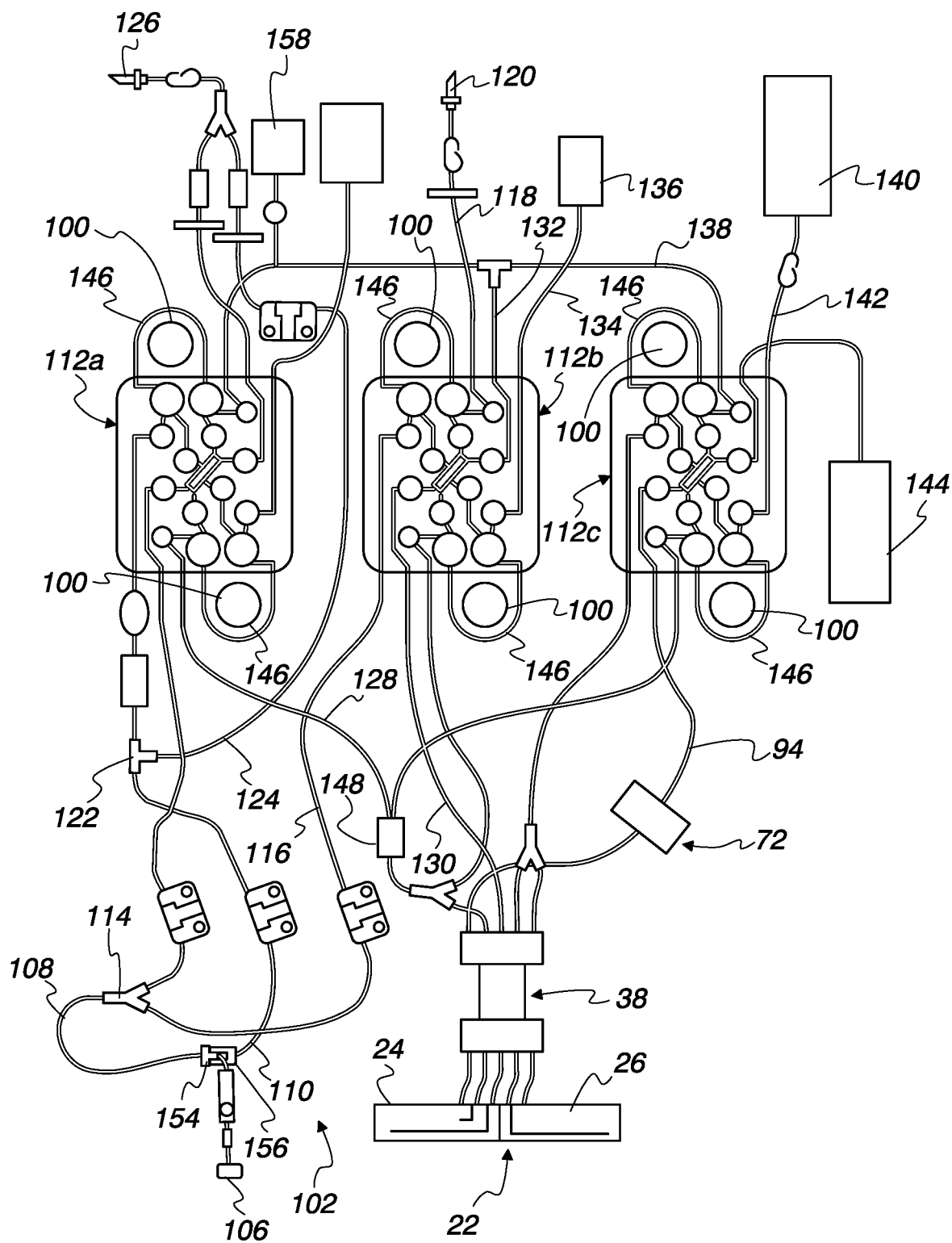
FIG. 14 illustrates the fluid processing assembly of FIG. 12, converted from the "double needle" configuration of FIG. 12 to an alternative "single needle" configuration.

One possible disruption to an MNC collection procedure (or any other procedure employing a fluid processing system 10 and fluid processing assembly 102 of the type described herein) renders one of the draw and return lines 108 and 110 inoperative (e.g., due to a blockage), while the other line remains viable. In this case, following termination, the incapacitated line may be directly connected to the viable line, with the procedure then continuing (in some capacity) with the fluid processing assembly 102 in a "single needle" configuration instead of a "double needle" configuration. FIGS. 13 and 14 illustrate two possible "single needle" configurations into which the fluid processing assembly 102 may be converted from its initial "double needle" configuration of FIG. 12.

In the configuration of FIG. 13, the return line 110 has been rendered inoperative, so it is directly connected to the draw line 108 for continued processing. The draw line 108 and return line 110 are provided with mating connectors 150 and 152 that are directly connected to convert the fluid processing assembly 102 from a "double needle" configuration to a "single needle" configuration in which the draw line 108 is responsible for both fluid draw and return. In the illustrated embodiment, the connector 150 of the draw line 108 is a configured as a female luer, while the connector 152 on the return line 110 is configured as a male luer, but the exact configuration of the mating connectors 150 and 152 may vary without departing from the scope of the present disclosure.

In the configuration of FIG. 14, the draw line 108 has been rendered inoperative, so it is directly connected to the return line 110 for continued processing. The draw line 108 and return line 110 are provided with mating connectors 154 and 156 that are directly connected to convert the fluid processing assembly 102 from a "double needle" configuration to a "single needle" configuration in which the return line 110 is responsible for both fluid draw and return. In the illustrated embodiment, the connector 154 of the draw line 108 is a configured as a male luer, while the connector 156 on the return line 110 is configured as a female luer, but the exact configuration of the mating connectors 154 and 156 may vary without departing from the scope of the present disclosure.

In general, a "single needle" procedure may include the same phases as a corresponding "double needle" procedure, but may require additional phases or sub-phases to account for the single access point to the fluid source. While a "double needle" configuration allows for simultaneous fluid draw and return, a "single needle" configuration requires alternating fluid draw and return via the single access line. Thus, when executing an MNC collection procedure using a fluid processing assembly 102 in a "single needle" configuration, the same phases of the above-described "double needle" configuration are carried out, but blood draw will be periodically suspended to allow for separated fluid components and/or other fluid (e.g., saline or another replacement fluid) to be conveyed to the blood source. The fluid processing assembly 102 may be provided with a return container 158 that is unused in the "double needle" configuration, but which provides a temporary reservoir for separated fluid components during blood draw of a "single needle" procedure, with the contents of the return container 158 subsequently being conveyed to the blood source during a return phase or sub-phase.

The processing following conversion from a "double needle" configuration to a "single needle" configuration may vary depending on a number of factors, including: the current procedure state or phase at the time of termination, the amount of fluid processed at the time of termination, the amount of fluid currently present in the fluid processing assembly 102 at the time of termination, and current fluid balance. The controller of the fluid processing system 10 may monitor at least one of these factors (and/or some other appropriate factor) and use that information to determine how to proceed once processing is unpaused. Depending on the circumstances, the controller may determine that it is appropriate to continue the procedure state or phase that was being executed at the time of termination. If the controller instead determines that it would be inappropriate to continue with the procedure state or phase that was being executed at the time of termination, then it may instead initiate a different procedure state or phase, which may be the phase or procedure state immediately following the phase or procedure state that was being executed at the time of termination, a variation of such succeeding phase or procedure state, or some other phase or procedure state.

For example, according to one approach, the fluid processing assembly 102 is disconnected from the fluid source upon mid-processing termination of an MNC collection procedure and converted from a "double needle" configuration into a "single needle" configuration, with the single access line (i.e., either the draw line 108 in the configuration of FIG. 13 or the return line 110 in the configuration of FIG. 14) being connected to a saline container. When a system operator or technician confirms that the fluid processing assembly 102 has been successfully converted to a "single needle" configuration, the controller may unpause processing by initiating a phase or procedure state in which saline is drawn into the fluid processing assembly 102 via the access line and used to convey blood and/or separated red blood cells in the fluid processing assembly 102 (e.g., in the draw and/or return lines 108 and 110, in the left cassette 112a, and/or in the middle cassette 112b) to the separation chamber 22. The blood conveyed into the separation chamber 22 may be used to accumulate an additional amount of MNCs within the separation chamber 22, while the red blood cells separated from the salvaged blood, along with the salvaged red blood cells conveyed into the separation chamber 22, may be directed out of the separation chamber 22 to the red blood cell collection container 136 for later use in harvesting MNCs.

Figure 15A:
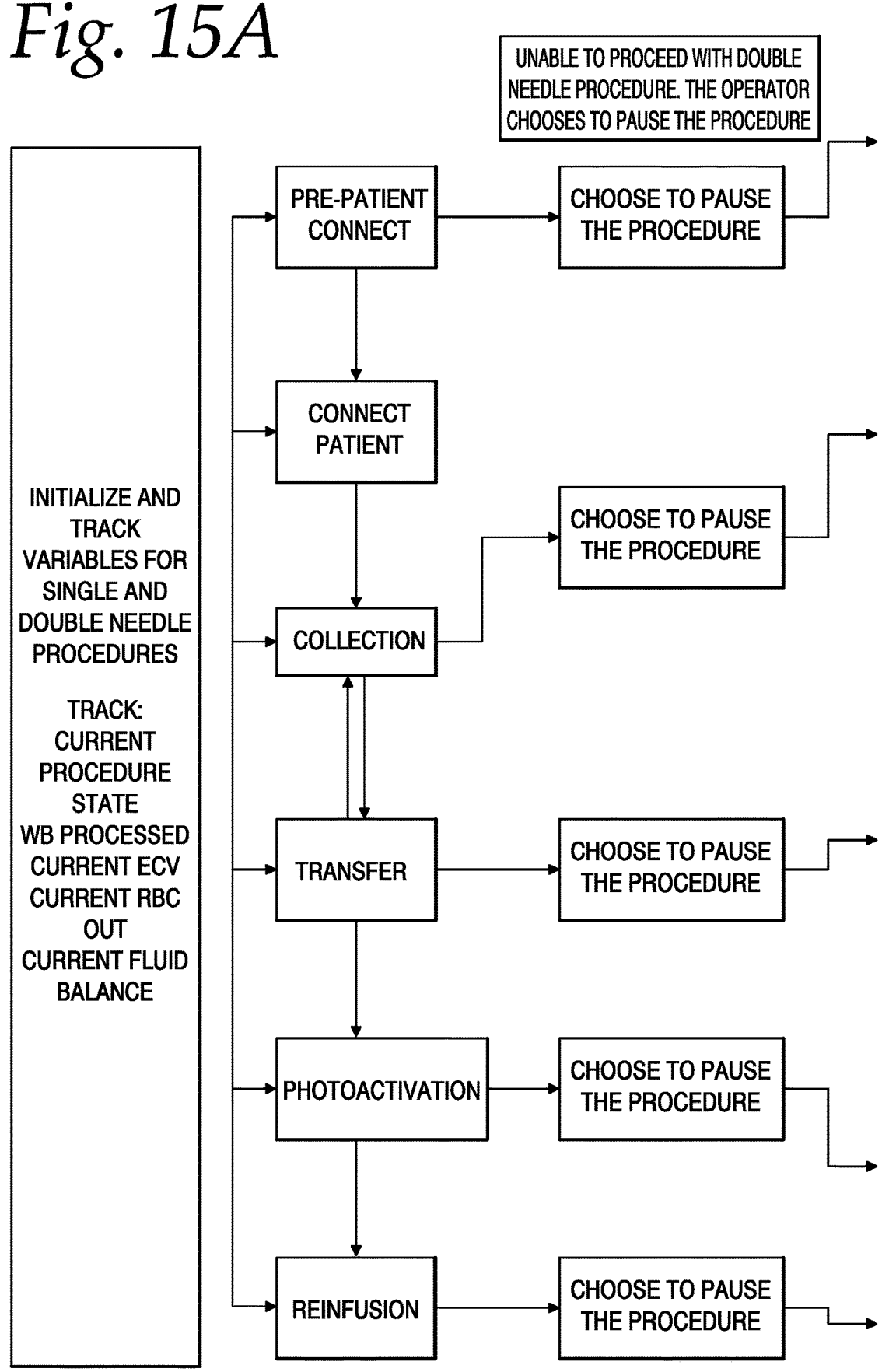
FIGS. 15A and 15B are parts of a flow chart showing possible options that a system controller has for proceeding following mid-procedure termination.
Figure 15B:
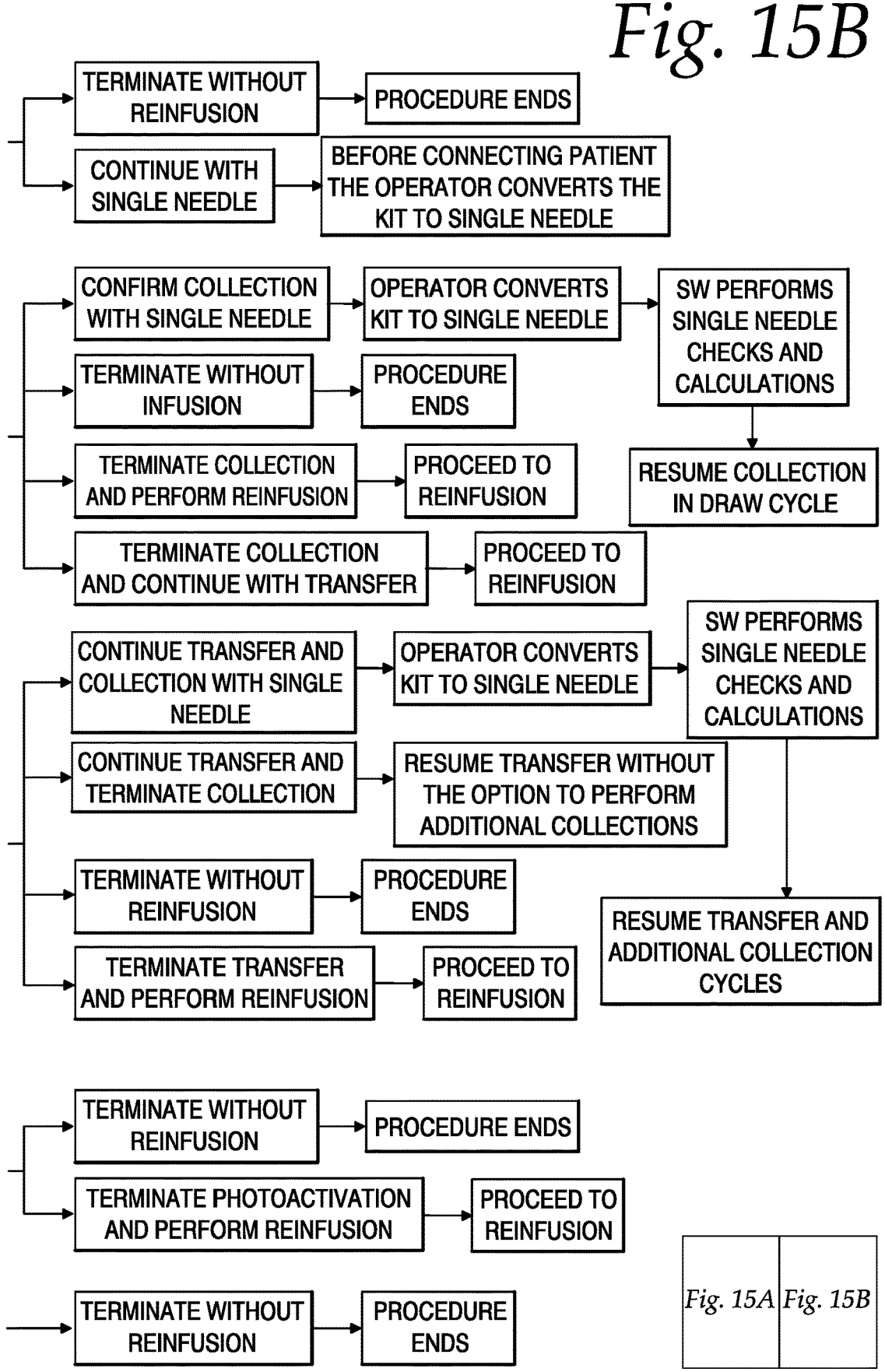

It should be understood that the preceding is only one exemplary approach to continuing a terminated MNC collection procedure, and that other approaches may also be employed without departing from the scope of the present disclosure. FIGS. 15A and 15B show one exemplary manner in which the system controller may be programmed with possible options for proceeding with a terminated procedure (which may include permanent termination of the procedure), depending on the current phase or procedure state being executed at the time of termination. As shown in FIGS. 15A and 15B, converting the fluid processing assembly 102 from a "double needle" configuration to a "single needle" configuration is only one possible approach to mid-processing termination, but may be advantageous for a relatively early termination, as it allows for completion (or at least substantial completion) of the intended procedure, whereas other approaches may result in a truncated version of the intended procedure.

For example, if processing is terminated during a "collection" procedure state, the controller has four options for proceeding. The first option is to continue the "collection" procedure state with the fluid processing assembly 102 in a "single needle" configuration instead of its initial "double needle" configuration. Once the operator or technician has converted the fluid processing assembly 102, the "collection" procedure state resumes in a "single needle" variation of the terminated "double needle" procedure state, with the procedure ultimately being completed with the fluid processing assembly 102 in a "single needle" configuration. If the controller determines that conversion is not an option (or if the operator or technician instructs the controller to not proceed with conversion), then the controller may either terminate the procedure without reinfusion (which ends the procedure), terminate the "collection" procedure state and perform reinfusion (which eliminates "transfer" and "photoactivation" procedure states), or terminate the partially completed "collection" procedure state and proceed with the succeeding "transfer" procedure state. As described above, the particular approach selected or recommended by the system controller may depend on one or more factors that are monitored by the controller during processing.

Similarly, if processing is terminated during a "transfer" procedure state, the controller has four options for proceeding. The first option is to continue the "transfer" procedure state with the fluid processing assembly 102 in a "single needle" configuration instead of its initial "double needle" configuration. Once the operator or technician has converted the fluid processing assembly 102, the "transfer" procedure state resumes in a "single needle" variation of the terminated "double needle" procedure state (including the option of performing additional "collection" phases), with the procedure ultimately being completed with the fluid processing assembly 102 in a "single needle" configuration. If the controller determines that conversion is not an option (or if the operator or technician instructs the controller to not proceed with conversion), then the controller may either terminate the procedure without reinfusion (which ends the procedure), terminate the "transfer" procedure state and perform reinfusion (which eliminates a "photoactivation" procedure state), or continue the "transfer" procedure state without the option of performing additional "collection" phases.

If processing is terminated earlier (during a "pre-patient connect" procedure state) or later (during a "photoactivation" or "reinfusion" procedure state), then the controller may have fewer options for proceeding. For example, if processing is terminated during a "pre-patient connect" procedure state, the controller has the option of either terminating the procedure or calling for the operator or technician to convert the fluid processing assembly 102 to a "single needle" configuration and proceeding with a "single needle" variation of the intended "double needle" procedure. If the procedure is terminated during a "photoactivation" procedure state, then the controller terminates the "photoactivation" procedure state, with the option of either terminating the procedure or proceeding to the succeeding "reinfusion" procedure state. Finally, if the procedure is terminated during the "reinfusion" procedure state, the controller only has the option of ending the procedure state and the procedure. Again, it should be understood that the programming represented by FIGS. 15A and 15B is merely exemplary, and that the system controller may be differently programmed without departing from the scope of the present disclosure.

Aspects

Aspect 1. A method for collecting mononuclear cells, comprising: separating red blood cells from blood in a separation chamber and conveying at least a portion of the separated red blood cells from the separation chamber to a red blood cell collection container; separating a mononuclear cell-containing layer from blood in the separation chamber while removing red blood cells from the separation chamber, recirculating at least a portion of the removed red blood cells through the separation chamber, and allowing a volume of the mononuclear cell-containing layer to increase in the separation chamber; and conveying at least a portion of the contents of the red blood cell collection container to the separation chamber to convey at least a portion of the mononuclear cell-containing layer out of the separation chamber for collection, wherein said at least a portion of the separated red blood cells are conveyed to the red blood cell collection container prior to recirculating said at least a portion of the removed red blood cells through the separation chamber.

Aspect 2. The method of Aspect 1, further comprising separating plasma from blood in the separation chamber and conveying at least a portion of the separated plasma from the separation chamber to a plasma collection container prior to conveying said at least a portion of the separated red blood cells to the red blood cell collection container.

Aspect 3. The method of any one of the preceding Aspects, further comprising determining whether a blood source has a minimum total blood volume and/or a minimum hematocrit, and upon determining that the blood source does not have the minimum total blood volume and/or the minimum hematocrit, recirculating said at least a portion of the removed red blood cells through the separation chamber prior to conveying said at least a portion of the separated red blood cells to the red blood cell collection container instead of after conveying said at least a portion of the separated red blood cells to the red blood cell collection container.

Aspect 4. A fluid processing system, comprising: a centrifuge configured to receive a separation chamber of a fluid processing assembly; a plurality of pumps configured to convey fluids through the fluid processing assembly; and a controller programmed to actuate the centrifuge to separate red blood cells from blood in the separation chamber and actuate at least one of the plurality of pumps to convey at least a portion of the separated red blood cells from the separation chamber to a red blood cell collection container of the fluid processing assembly, actuate the centrifuge to separate a mononuclear cell-containing layer from blood in the separation chamber while actuating at least one of the plurality of pumps to remove red blood cells from the separation chamber, actuating at least one of the plurality of pumps to recirculate at least a portion of the removed red blood cells through the separation chamber, and allowing a volume of the mononuclear cell-containing layer to increase in the separation chamber, and actuate at least one of the plurality of pumps to convey at least a portion of the contents of the red blood cell collection container to the separation chamber to convey at least a portion of the mononuclear cell-containing layer out of the separation chamber for collection, wherein the controller is programmed such that said at least a portion of the separated red blood cells are conveyed to the red blood cell collection container prior to recirculating said at least a portion of the removed red blood cells through the separation chamber.

Aspect 5. The fluid processing system of Aspect 4, wherein the controller is further programmed to actuate the centrifuge to separate plasma from blood in the separation chamber, and actuate at least one of the plurality of pumps to convey at least a portion of the separated plasma from the separation chamber to a plasma collection container of the fluid processing assembly prior to conveying said at least a portion of the separated red blood cells to the red blood cell collection container.

Aspect 6. The fluid processing system of any one of Aspects 4-5, wherein the controller is further programmed to determine whether a blood source has a minimum total blood volume and/or a minimum hematocrit, and upon determining that the blood source does not have the minimum total blood volume and/or the minimum hematocrit, actuate at least one of the plurality of pumps to recirculate said at least a portion of the removed red blood cells through the separation chamber prior to conveying said at least a portion of the separated red blood cells to the red blood cell collection container instead of after conveying said at least a portion of the separated red blood cells to the red blood cell collection container.

Aspect 7. A method for collecting mononuclear cells, comprising: conveying blood to a red blood cell collection container; separating a mononuclear cell-containing layer from blood in a separation chamber while removing red blood cells from the separation chamber, recirculating at least a portion of the removed red blood cells through the separation chamber, and allowing a volume of the mononuclear cell-containing layer to increase in the separation chamber; and conveying at least a portion of the contents of the red blood cell collection container to the separation chamber to convey at least a portion of the mononuclear cell-containing layer out of the separation chamber for collection, wherein blood is conveyed to the red blood cell collection container prior to recirculating said at least a portion of the removed red blood cells through the separation chamber.

Aspect 8. The method of Aspect 7, wherein said conveying blood to the red blood cell collection container comprises conveying a first portion of blood to the red blood cell collection container while simultaneously conveying a second portion of blood to the separation chamber.

Aspect 9. The method of Aspect 8, further comprising separating plasma from the second portion of blood in the separation chamber and conveying at least a portion of the separated plasma from the separation chamber to a plasma collection container while conveying the first portion of blood to the red blood cell collection container.

Aspect 10. The method of Aspect 7, wherein blood is conveyed to the red blood cell collection container prior to blood being conveyed to the separation chamber.

Aspect 11. The method of any one of Aspects 7-10, further comprising determining whether a blood source has a minimum total blood volume and/or a minimum hematocrit, and upon determining that the blood source does not have the minimum total blood volume and/or the minimum hematocrit, conveying blood to the separation chamber and not to the red blood cell collection container.

Aspect 12. A fluid processing system, comprising: a centrifuge configured to receive a separation chamber of a fluid processing assembly; a plurality of pumps configured to convey fluids through the fluid processing assembly; and a controller programmed to actuate at least one of the plurality of pumps to convey blood to a red blood cell collection container of the fluid processing assembly, actuate the centrifuge to separate a mononuclear cell-containing layer from blood in the separation chamber while actuating at least one of the plurality of pumps to remove red blood cells from the separation chamber, actuating at least one of the plurality of pumps to recirculate at least a portion of the removed red blood cells through the separation chamber, and allowing a volume of the mononuclear cell-containing layer to increase in the separation chamber, and actuate at least one of the plurality of pumps to convey at least a portion of the contents of the red blood cell collection container to the separation chamber to convey at least a portion of the mononuclear cell-containing layer out of the separation chamber for collection, wherein the controller is programmed such that blood is conveyed to the red blood cell collection container prior to recirculating said at least a portion of the removed red blood cells through the separation chamber.

Aspect 13. The fluid processing system of Aspect 12, wherein said actuating at least one of the plurality of pumps to convey blood to the red blood cell collection container comprises actuating at least one of the plurality of pumps to convey a first portion of blood to the red blood cell collection container while simultaneously conveying a second portion of blood to the separation chamber.

Aspect 14. The fluid processing system of Aspect 13, wherein the controller is further programmed to actuate the centrifuge to separate plasma from the second portion of blood in the separation chamber, and actuate at least one of the plurality of pumps to convey at least a portion of the separated plasma from the separation chamber to a plasma collection container of the fluid processing assembly while conveying the first portion of blood to the red blood cell collection container.

Aspect 15. The fluid processing system of Aspect 12, wherein the controller is programmed such that blood is conveyed to the red blood cell collection container prior to blood being conveyed to the separation chamber.

Aspect 16. The fluid processing system of any one of Aspects 12-15, wherein the controller is further programmed to determine whether a blood source has a minimum total blood volume and/or a minimum hematocrit, and upon determining that the blood source does not have the minimum total blood volume and/or the minimum hematocrit, actuate the at least one of the plurality of pumps to convey blood to the separation chamber and not to the red blood cell collection container.

Aspect 17. A method for collecting mononuclear cells, comprising: conveying blood through a cassette and a drip chamber of a fluid processing assembly to a separation chamber of the fluid processing assembly; separating a mononuclear cell-containing layer from the blood in the separation chamber and removing other blood components from the separation chamber while a volume of the mononuclear cell-containing layer increases in the separation chamber; conveying blood from the cassette and/or the drip chamber to a red blood cell collection container of the fluid processing assembly; and conveying at least a portion of the contents of the red blood cell collection container to the separation chamber to convey at least a portion of the mononuclear cell-containing layer out of the separation chamber for collection.

Aspect 18. A fluid processing system, comprising: a centrifuge configured to receive a separation chamber of a fluid processing assembly; a plurality of pumps configured to convey fluids through the fluid processing assembly; and a controller programmed to actuate at least one of the plurality of pumps to convey blood through a cassette and a drip chamber of the fluid processing assembly to the separation chamber, actuate the centrifuge to separate a mononuclear cell-containing layer from blood in the separation chamber while actuating at least one of the plurality of pumps to remove other blood components from the separation chamber, and allowing a volume of the mononuclear cell-containing layer to increase in the separation chamber, actuate at least one of the plurality of pumps to convey blood from the cassette and/or the drip chamber to a red blood cell collection container of the fluid processing assembly, and actuate at least one of the plurality of pumps to convey at least a portion of the contents of the red blood cell collection container to the separation chamber to convey at least a portion of the mononuclear cell-containing layer out of the separation chamber for collection.

Aspect 19. A method for collecting mononuclear cells, comprising: conveying blood through a first cassette of a fluid processing assembly to a separation chamber of the fluid processing assembly; separating a mononuclear cell-containing layer and red blood cells from the blood in the separation chamber and conveying at least a portion of the red blood cells out of the separation chamber and through a second cassette of the fluid processing assembly while a volume of the mononuclear cell-containing layer increases in the separation chamber; conveying saline through the first cassette and/or the second cassette to convey blood and/or red blood cells from the first cassette and/or the second cassette to a red blood cell collection container of the fluid processing assembly; and conveying at least a portion of the contents of the red blood cell collection container to the separation chamber to convey at least a portion of the mononuclear cell-containing layer out of the separation chamber for collection.

Aspect 20. A fluid processing system, comprising: a centrifuge configured to receive a separation chamber of a fluid processing assembly; a plurality of pumps configured to convey fluids through the fluid processing assembly; and a controller programmed to actuate at least one of the plurality of pumps to convey blood through a first cassette of a fluid processing assembly to the separation chamber, actuate the centrifuge to separate a mononuclear cell-containing layer and red blood cells from blood in the separation chamber while actuating at least one of the plurality of pumps to convey at least a portion of the red blood cells out of the separation chamber and through a second cassette of the fluid processing assembly, and allowing a volume of the mononuclear cell-containing layer to increase in the separation chamber, actuate at least one of the plurality of pumps to convey saline through the first cassette and/or the second cassette to convey blood and/or red blood cells from the first cassette and/or the second cassette to a red blood cell collection container of the fluid processing assembly, and actuate at least one of the plurality of pumps to convey at least a portion of the contents of the red blood cell collection container to the separation chamber to convey at least a portion of the mononuclear cell-containing layer out of the separation chamber for collection.

Aspect 21. A fluid processing assembly configured for use in combination with a fluid processing system, comprising: a separation chamber configured to separate a fluid into two or more fluid components and including an inlet flow path and an outlet flow path; a draw line in fluid communication with the inlet flow path and configured for direct connection to a source to draw a fluid from the source into the fluid processing assembly; and a return line in fluid communication with the outlet flow path and configured for direct connection to the source to convey a replacement fluid and/or at least a portion of a separated fluid component to the source, wherein the draw line includes a first connector, the return line includes a second connector configured to be connected to the first connector, and connecting the first and second connectors removes one of the draw and return lines from direct connection to the source while placing the other one of the draw and return lines into condition for drawing fluid from the source into the fluid processing assembly and conveying a replacement fluid and/or at least a portion of a separated fluid component to the source.

Aspect 22. The fluid processing assembly of Aspect 21, wherein connecting the first and second connectors removes the draw line from direct connection to the source while placing the return line into condition for drawing fluid from the source into the fluid processing assembly and conveying a replacement fluid and/or at least a portion of a separated fluid component to the source.

Aspect 23. The fluid processing assembly of Aspect 21, wherein connecting the first and second connectors removes the return line from direct connection to the source while placing the draw line into condition for drawing fluid from the source into the fluid processing assembly and conveying a replacement fluid and/or at least a portion of a separated fluid component to the source.

Aspect 24. The fluid processing assembly of Aspect 21, wherein the draw line includes a third connector, the return line includes a fourth connector configured to be connected to the third connector, connecting the first and second connectors removes the return line from direct connection to the source while placing the draw line into condition for drawing fluid from the source into the fluid processing assembly and conveying a replacement fluid and/or at least a portion of a separated fluid component to the source, and connecting the third and fourth connectors removes the draw line from direct connection to the source while placing the return line into condition for drawing fluid from the source into the fluid processing assembly and conveying a replacement fluid and/or at least a portion of a separated fluid component to the source.

Aspect 25. The fluid processing assembly of any one of Aspects 21-24, wherein one of the first and second connectors comprises a female luer and the other one of the first and second connectors comprises a male luer.

Aspect 26. The fluid processing assembly of any one of Aspects 21-25, further comprising a return container configured to be used during a procedure following connection of the first and second connectors and not during a procedure before connection of the first and second connectors.

Aspect 27. A method for processing a fluid, comprising: directly connecting a draw line and a return line of a fluid processing assembly to a source; drawing fluid from the source into the fluid processing assembly via the draw line; processing at least a portion of the fluid within the fluid processing assembly; pausing processing of said at least a portion of the fluid; directly connecting the draw line and the return line so as to remove one of the draw and return lines from direct connection to the source; and unpausing processing.

Aspect 28. The method of Aspect 27, wherein said unpausing processing comprises drawing an additional amount of fluid from the source into the fluid processing assembly via the other one of the draw and return lines and processing at least a portion of said additional amount of fluid within the fluid processing assembly, and/or conveying a replacement fluid and/or at least a portion of the processed fluid to the source via the other one of the draw and return lines.

Aspect 29. The method of any one of Aspects 27-28, wherein the return line is removed from direct connection to the source.

Aspect 30. The method of any one of Aspects 27-28, wherein the draw line is removed from direct connection to the source.

Aspect 31. The method of any one of Aspects 27-30, further comprising monitoring at least one of a current procedure state, an amount of fluid processed, an amount of fluid currently present in the fluid processing assembly, an amount of a fluid constituent currently present in the fluid processing assembly, and current fluid balance, and determining how to proceed upon said unpausing processing based at least in part on said monitored value(s).

Aspect 32. The method of any one of Aspects 27-31, wherein said pausing processing includes pausing during a procedure state, and said unpausing processing includes continuing the procedure state.

Aspect 33. The method of any one of Aspects 27-31, wherein said pausing processing includes pausing during a procedure state, and said unpausing processing includes initiating a different procedure state and not continuing the procedure state.

Aspect 34. The method of any one of Aspects 27-33, wherein said directly connecting the draw line and the return line so as to remove one of the draw and return lines from direct connection to the source includes connecting a female luer to a male luer.

Aspect 35. The method of any one of Aspects 27-34, further comprising conveying at least a portion of the processed fluid into a return container after the draw and return lines are connected and not before the draw and return lines are connected.

Aspect 36. A method for processing a fluid, comprising: providing a fluid processing assembly including a draw line and a return line each configured to be directly connected to a source; directly connecting the draw line and the return line so as to prevent one of the draw and return lines from being directly connected to the source; directly connecting the other one of the draw and return lines to the source; drawing fluid from the source into the fluid processing assembly via the other one of the draw and return lines; and processing at least a portion of the fluid within the fluid processing assembly.

Aspect 37. The method of Aspect 36, wherein the return line is removed from direct connection to the source.

Aspect 38. The method of any one of Aspects 36-37, wherein the draw line is removed from direct connection to the source.

Aspect 39. The method of any one of Aspects 36-38, wherein said directly connecting the draw line and the return line so as to remove one of the draw and return lines from direct connection to the source includes connecting a female luer to a male luer.

Aspect 40. The method of any one of Aspects 36-39, further comprising conveying at least a portion of the processed fluid into a return container of the fluid processing assembly that is not configured to receive fluid during a procedure in which the draw and return lines are not directly connected.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A method for collecting mononuclear cells, comprising:
conveying blood through a first cassette of a fluid processing assembly to a separation chamber of the fluid processing assembly;

separating a mononuclear cell-containing layer and red blood cells from the blood in the separation chamber and conveying at least a portion of the red blood cells out of the separation chamber and through a second cassette of the fluid processing assembly while a volume of the mononuclear cell-containing layer increases in the separation chamber;

conveying saline through the first cassette and/or the second cassette to convey blood and/or red blood cells from the first cassette and/or the second cassette to a red blood cell collection container of the fluid processing assembly; and conveying at least a portion of the contents of the red blood cell collection container to the separation chamber to convey at least a portion of the mononuclear cell-containing layer out of the separation chamber for collection.

2. The method of claim 1, further comprising separating plasma from blood in the separation chamber and conveying at least a portion of the separated plasma out of the separation chamber while conveying said at least a portion of the separated red blood cells out of the separation chamber.

3. The method of claim 2, wherein said at least a portion of the separated plasma is conveyed out of the separation chamber and through a third cassette of the fluid processing assembly.

4. The method of claim 3, wherein said at least a portion of the separated plasma is conveyed through the third cassette, through the first cassette, and to a blood source.

5. The method of claim 3, wherein said at least a portion of the separated plasma is conveyed through the third cassette and to the separation chamber.

6. The method of claim 3, wherein said at least a portion of the separated plasma is conveyed through the third cassette and to a plasma collection container of the fluid processing assembly.

7. The method of claim 1, wherein said at least a portion of the red blood cells is conveyed out of the separation chamber, through the second cassette, and to a blood source.

8. The method of claim 7, wherein said at least a portion of the red blood cells is conveyed through the first cassette after being conveyed through the second cassette and before being conveyed to the blood source.

9. The method of claim 1, wherein said at least a portion of the red blood cells is conveyed out of the separation chamber, through the second cassette, and to the red blood cell collection container.

10. The method of claim 1, wherein said at least a portion of the red blood cells is conveyed out of the separation chamber, through the second cassette, and back to the separation chamber.

11. A fluid processing system, comprising:
a centrifuge configured to receive a separation chamber of a fluid processing assembly;
a plurality of pumps configured to convey fluids through the fluid processing assembly; and
a controller programmed to
actuate at least one of the plurality of pumps to convey blood through a first cassette of a fluid processing assembly to the separation chamber,
actuate the centrifuge to separate a mononuclear cell-containing layer and red blood cells from blood in the separation chamber while
actuating at least one of the plurality of pumps to convey at least a portion of the red blood cells out of the separation chamber and through a second cassette of the fluid processing assembly, and
allowing a volume of the mononuclear cell-containing layer to increase in the separation chamber,
actuate at least one of the plurality of pumps to convey saline through the first cassette and/or the second cassette to convey blood and/or red blood cells from the first cassette and/or the second cassette to a red blood cell collection container of the fluid processing assembly, and
actuate at least one of the plurality of pumps to convey at least a portion of the contents of the red blood cell collection container to the separation chamber to convey at least a portion of the mononuclear cell-containing layer out of the separation chamber for collection.

12. The fluid processing system of claim 11, wherein the controller is further programmed to
actuate the centrifuge to separate plasma from blood in the separation chamber, and
actuate at least one of the plurality of pumps to convey at least a portion of the separated plasma out of the separation chamber while conveying said at least a portion of the separated red blood cells out of the separation chamber.

13. The fluid processing system of claim 12, wherein said at least a portion of the separated plasma is conveyed out of the separation chamber and through a third cassette of the fluid processing assembly.

14. The fluid processing system of claim 13, wherein said at least a portion of the separated plasma is conveyed through the third cassette, through the first cassette, and to a blood source.

15. The fluid processing system of claim 13, wherein said at least a portion of the separated plasma is conveyed through the third cassette and to the separation chamber.

16. The fluid processing system of claim 13, wherein said at least a portion of the separated plasma is conveyed through the third cassette and to a plasma collection container of the fluid processing assembly.

17. The fluid processing system of claim 11, wherein the controller is programmed to actuate said at least one of the plurality of pumps to convey said at least a portion of the red blood cells out of the separation chamber, through the second cassette, and to a blood source.

18. The fluid processing system of claim 17, wherein the controller is programmed to actuate said at least one of the plurality of pumps to convey said at least a portion of the red blood cells through the first cassette after being conveyed through the second cassette and before being conveyed to the blood source.

19. The fluid processing system of claim 11, wherein the controller is programmed to actuate said at least one of the plurality of pumps to convey said at least a portion of the red blood cells out of the separation chamber, through the second cassette, and to the red blood cell collection container.

20. The fluid processing system of claim 11, wherein the controller is programmed to actuate said at least one of the plurality of pumps to convey said at least a portion of the red blood cells out of the separation chamber, through the second cassette, and back to the separation chamber.

* * * * *